United States Patent
Wang et al.

(10) Patent No.: US 8,614,182 B2
(45) Date of Patent: Dec. 24, 2013

(54) GLP-1 ANALOGUES AND THEIR PHARMACEUTICAL SALTS AND USES

(75) Inventors: Yali Wang, Jiangsu (CN); Aifeng Lü, Jiangsu (CN); Changan Sun, Jiangsu (CN); Hengli Yuan, Jiangsu (CN)

(73) Assignee: Jiangsu Hansoh Pharmaceuticals Co., Ltd., Lianyungang, Jiangsu (CN)

( * ) Notice: Subject to any disclaimer, the term of this patent is extended or adjusted under 35 U.S.C. 154(b) by 11 days.

(21) Appl. No.: 13/362,593

(22) Filed: Jan. 31, 2012

(65) Prior Publication Data

US 2012/0196798 A1  Aug. 2, 2012

Related U.S. Application Data

(63) Continuation of application No. 13/388,056, filed as application No. PCT/CN2010/075548 on Jul. 29, 2010.

(30) Foreign Application Priority Data

Jul. 30, 2009 (CN) .......................... 2009 1 0165559

(51) Int. Cl.
| | |
|---|---|
| A61K 38/26 | (2006.01) |
| A61K 38/00 | (2006.01) |
| A61K 38/16 | (2006.01) |
| A61K 38/12 | (2006.01) |
| C07K 1/00 | (2006.01) |

(52) U.S. Cl.
USPC ............. 514/7.2; 514/6.9; 514/7.3; 514/21.3; 530/308; 530/324; 530/402

(58) Field of Classification Search
None
See application file for complete search history.

(56) References Cited

U.S. PATENT DOCUMENTS

| | | | |
|---|---|---|---|
| 5,424,286 A | 6/1995 | Eng | |
| 5,545,618 A | 8/1996 | Buckley et al. | |
| 6,528,486 B1 * | 3/2003 | Larsen et al. ................... | 514/6.8 |
| 7,226,990 B2 * | 6/2007 | Knudsen et al. ............... | 530/308 |
| 2003/0199672 A1 | 10/2003 | Knudsen et al. | |
| 2008/0207507 A1 | 8/2008 | Lau et al. | |
| 2010/0048468 A1 | 2/2010 | Gegg, Jr. et al. | |

FOREIGN PATENT DOCUMENTS

| | | |
|---|---|---|
| CN | 1232470 A | 10/1999 |
| CN | 101128214 A | 2/2008 |
| WO | WO 98/08871 | 3/1998 |
| WO | WO 2007/124461 A2 | 11/2007 |

OTHER PUBLICATIONS

Ferrannini E., "Insulin Resistance versus Insulin Deficiency in Non-Insulin-Dependent Diabetes Mellitus: Problems and Prospects," *Endocrine Reviews* 1998, 19(4): 477-490.

Weyer, C. et al., "The Natural History of Insulin Secretory Dysfunction and Insulin Resistance in the Pathogenesis of Type 2 Diabetes Mellitus," *Journal of Clinical Invest.* 1999, 104:787-794.

Drucker, Daniel J., "Enhancing Incretin Action for the Treatment of Type 2 Diabetes," *Diabetes Care*, 2003, vol. 26 (10):2929-2940.

Deacon, Carolyn F. et al., "Both Subcutaneously and Intravenously Administered Glucagon-like Peptide I are Rapidly Degraded from the NH2-terminus in Type II Diabetic Patients and in Healthy Subjects," *Diabetes*, 1995, 44.9:1126-1131.

Gallwitz, Baptist, "Glucagon-Like Peptide-l-Based Therapies for the Treatment of Type 2 Diabetes Mellitus," *Treatments in Endocrinology*, 2005, 4 (6); 361-370.

Li, Yazhou et al., "Glucagon-Like Peptide-1 Receptor Signaling Modulates Beta Cell Apoptosis," *The Journal of Biological Chemistry*, 2003, vol. 278(1): 471-478.

Deacon, Carolyn F., "Therapeutic Strategies Based on Glucagon-Like Peptide 1," *Diabetes*, 2004, 53(9): 2181-2189.

Toft-Nielson, Mai-Britt et al., "Determinants of the Impaired Secretion of Glucagon-Like Peptide-1 in Type 2 Diabetic Patients," *The Journal of Clinical Endocrinology & Metabolism* 2001, 86(8): 3717-3723.

Drucker, Daniel J. et al., "The Incretin System: Glucagon-Like Peptide-1 Receptor Agonists and Dipeptidyl Peptidase-4 Inhibitors in Type 2 Diabetes," *The Lancet* 2006, 368(9548): 1696-1705.

Kolterman, Orville G. et al., "Pharmacokinetics, Pharmacodynamics, and Safety of Exenatide in Patients with Type 2 Diabetes Mellitus," *Am J Health-Syst Pharm.* 2005, 62(2): 173-181.

Nielsen, Loretta L. et al., "Pharmacology of Exenatide (Synthetic Exendin-4) for the Treatment of Type 2 Diabetes," *Current Drugs*, 2003, 4(4): 401-405.

Kim, Jung-Guk et al., "Development and Characterization of a Glucagon-Like Peptide 1-Albumin Conjugate: The Ability to Activate the Glucagon-Like Peptide 1 Receptor in Vivo," *Diabetes*, 2003, 52(3): 751-759.

Baggio, Laurie L. et al., "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," *Diabetes*, 2004, 53(9): 2492-2500.

Nielsen, Loretta L. et al., "Pharmacology of Exenatide (Synthetic Exendin-4): A Potential Therapeutic for Improved Glycemic Control of Type 2 Diabetes," *Regulatory Peptides*, 2004, 77-88.

* cited by examiner

*Primary Examiner* — Shulamith H Shafer
(74) *Attorney, Agent, or Firm* — Ryan L. Marshall; Brinks Gilson & Lione

(57) ABSTRACT

This invention discloses GLP-1 analogues and their pharmaceutical salts, wherein the GLP-1 analogue comprises an amino acid sequence of general formula (I), wherein Lys represents a modified lysine with a lipophilic acid. The GLP-1 analogues provided by this invention have the function of human GLP-1, and a longer half-life in vivo compared with the human GLP-1. Uses of such compounds and compositions include treating non-insulin-dependent diabetes, insulin-dependent diabetes, and obesity.

$X_1$-$X_2$-Glu-Gly-Thr-Phe-Thr-Ser-Asp-$X_{10}$-Ser-$X_{12}$-$X_{13}$-$X_{14}$-Glu-$X_{16}$-$X_{17}$-Ala-$X_{19}$-$X_{20}$-$X_{21}$-Phe-Ile-$X_{24}$-Trp-Leu-$X_{27}$-$X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-Lys   Formula (I)—SEQ ID NO: 238

51 Claims, No Drawings

SEQUENCE LISTING

```
<160> NUMBER OF SEQ ID NOS: 238

<210> SEQ ID NO 1
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: D-Ala

<400> SEQUENCE: 1

His Xaa Glu Gly Thr Phe Thr Ser Asp Leu Ser Lys Gln Asn Leu Glu
1               5                   10                  15

Glu Glu Glu Ala Val Arg Leu Phe Ile Glu Trp Leu Lys Gln Gly Gly
            20                  25                  30

Pro Ser Ser Gly Ala Pro Pro Pro Ser Lys
        35                  40

<210> SEQ ID NO 2
<211> LENGTH: 40
<212> TYPE: PRT
<213> ORGANISM: Artificial Sequence
<220> FEATURE:
<223> OTHER INFORMATION: Synthetic Peptide
```

```
<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 3
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: D-Ala

<400> SEQUENCE: 3

His Xaa Glu Gly Thr Phe Thr Ser Asp Val Ser Ser Tyr Leu Glu Glu
1               5                   10                  15

Glu Ala Ala Lys Glu Phe Ile Ala Trp Leu Val Arg Gly Gly Pro Ser
            20                  25                  30

Ser Gly Ala Pro Pro Pro Ser Lys
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib

<400> SEQUENCE: 4

His Xaa Glu Gly Thr Phe Thr Ser Asp Val Ser Ser Tyr Leu Glu Glu
1               5                   10                  15

Glu Ala Ala Lys Glu Phe Ile Ala Trp Leu Val Arg Gly Gly Pro Ser
            20                  25                  30

Ser Gly Ala Pro Pro Pro Ser Lys
        35                  40

<210> SEQ ID NO 5
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 5

His Ala Glu Gly Thr Phe Thr Ser Asp Val Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35
```

```
<210> SEQ ID NO 6
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 6

His Ala Glu Gly Thr Phe Thr Ser Asp Val Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 7

His Ala Glu Gly Thr Phe Thr Ser Asp Val Ser Ser Tyr Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 8
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 8

His Ala Glu Gly Thr Phe Thr Ser Asp Val Ser Ser Tyr Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
```

```
<400> SEQUENCE: 9

His Ala Glu Gly Thr Phe Thr Ser Asp Val Ser Ser Tyr Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 10

His Ala Glu Gly Thr Phe Thr Ser Asp Val Ser Ser Tyr Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 11

His Ala Glu Gly Thr Phe Thr Ser Asp Val Ser Ser Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 12

His Ala Glu Gly Thr Phe Thr Ser Asp Val Ser Ser Tyr Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 13
<211> LENGTH: 39
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 13

His Ala Glu Gly Thr Phe Thr Ser Asp Val Ser Ser Tyr Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 14

His Ala Glu Gly Thr Phe Thr Ser Asp Val Ser Ser Tyr Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 15

His Ala Glu Gly Thr Phe Thr Ser Asp Val Ser Ser Tyr Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 16

His Ala Glu Gly Thr Phe Thr Ser Asp Val Ser Ser Gln Leu Glu Gly
```

```
                    1               5                   10                  15
Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 17

His Ala Glu Gly Thr Phe Thr Ser Asp Val Ser Ser Gln Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 18

His Ala Glu Gly Thr Phe Thr Ser Asp Val Ser Ser Gln Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 19

His Ala Glu Gly Thr Phe Thr Ser Asp Val Ser Ser Gln Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (16)..(16)
<223> OTHER INFORMATION: Xaa: Aib

<400> SEQUENCE: 20

His Ala Glu Gly Thr Phe Thr Ser Asp Val Ser Ser Gln Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 21

His Ala Glu Gly Thr Phe Thr Ser Asp Val Ser Ser Gln Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 22

His Ala Glu Gly Thr Phe Thr Ser Asp Val Ser Ser Gln Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 23

His Ala Glu Gly Thr Phe Thr Ser Asp Val Ser Ser Gln Met Glu Gly
1               5                   10                  15

Gln Ala Ala Glu Phe Ile Val Trp Leu Val Lys Gly Arg Gly Lys Lys
```

```
                20                  25                  30

Gly Xaa Pro Pro Pro Ser Lys
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 24

His Ala Glu Gly Thr Phe Thr Ser Asp Val Ser Ser Gln Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 25

His Ala Glu Gly Thr Phe Thr Ser Asp Val Ser Ser Gln Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 26

His Ala Glu Gly Thr Phe Thr Ser Asp Val Ser Ser Gln Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
```

```
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 27

His Ala Glu Gly Thr Phe Thr Ser Asp Val Ser Ser Gln Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 28
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 28

His Ala Glu Gly Thr Phe Thr Ser Asp Val Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 29

His Ala Glu Gly Thr Phe Thr Ser Asp Val Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 30

His Ala Glu Gly Thr Phe Thr Ser Asp Val Ser Lys Tyr Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 31
```

```
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 31

His Ala Glu Gly Thr Phe Thr Ser Asp Val Ser Lys Tyr Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 32

His Ala Glu Gly Thr Phe Thr Ser Asp Val Ser Lys Tyr Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 33

His Ala Glu Gly Thr Phe Thr Ser Asp Val Ser Lys Tyr Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 34
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 34
```

His Ala Glu Gly Thr Phe Thr Ser Asp Val Ser Lys Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 35
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 35

His Ala Glu Gly Thr Phe Thr Ser Asp Val Ser Lys Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 36

His Ala Glu Gly Thr Phe Thr Ser Asp Val Ser Lys Tyr Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 37

His Ala Glu Gly Thr Phe Thr Ser Asp Val Ser Lys Tyr Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 38
<211> LENGTH: 39
<212> TYPE: PRT
<213> ORGANISM: Artificial Sequence

```
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 38

His Ala Glu Gly Thr Phe Thr Ser Asp Val Ser Lys Tyr Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 39
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 39

His Ala Glu Gly Thr Phe Thr Ser Asp Val Ser Lys Tyr Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 40
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 40

His Ala Glu Gly Thr Phe Thr Ser Asp Val Ser Lys Gln Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 41
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 41

His Ala Glu Gly Thr Phe Thr Ser Asp Val Ser Lys Gln Leu Glu Gly
1               5                   10                  15
```

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 42
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 42

His Ala Glu Gly Thr Phe Thr Ser Asp Val Ser Lys Gln Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 43
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 43

His Ala Glu Gly Thr Phe Thr Ser Asp Val Ser Lys Gln Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 44
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 44

His Ala Glu Gly Thr Phe Thr Ser Asp Val Ser Lys Gln Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 45
<211> LENGTH: 39
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 45

His Ala Glu Gly Thr Phe Thr Ser Asp Val Ser Lys Gln Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 46

His Ala Glu Gly Thr Phe Thr Ser Asp Val Ser Lys Gln Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 47
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 47

His Ala Glu Gly Thr Phe Thr Ser Asp Val Ser Lys Gln Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 48

His Ala Glu Gly Thr Phe Thr Ser Asp Val Ser Lys Gln Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35
```

```
<210> SEQ ID NO 49
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 49

His Ala Glu Gly Thr Phe Thr Ser Asp Val Ser Lys Gln Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 50

His Ala Glu Gly Thr Phe Thr Ser Asp Val Ser Lys Gln Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 51
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 51

His Ala Glu Gly Thr Phe Thr Ser Asp Val Ser Lys Gln Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 52
<211> LENGTH: 39
<212> TYPE: PRT
<213> ORGANISM: Artificial Sequence
<220> FEATURE:
<223> OTHER INFORMATION: Synthetic Peptide
```

-continued

```
<400> SEQUENCE: 52

His Ala Glu Gly Thr Phe Thr Ser Asp Leu Ser Lys Gln Leu Glu Gly
1               5                   10                  15
Gln Ala Ala Glu Phe Ile Val Trp Leu Val Lys Gly Arg Gly Lys Lys
            20                  25                  30
Gly Gly Pro Pro Pro Ser Lys
        35

<210> SEQ ID NO 53
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 53

His Ala Glu Gly Thr Phe Thr Ser Asp Leu Ser Lys Gln Leu Glu Gly
1               5                   10                  15
Gln Ala Ala Glu Phe Ile Val Trp Leu Val Lys Gly Arg Gly Lys Lys
            20                  25                  30
Gly Xaa Pro Pro Pro Ser Lys
        35

<210> SEQ ID NO 54
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 54

His Ala Glu Gly Thr Phe Thr Ser Asp Leu Ser Lys Gln Leu Glu Glu
1               5                   10                  15
Gln Ala Ala Glu Phe Ile Val Trp Leu Val Lys Gly Arg Gly Lys Lys
            20                  25                  30
Gly Gly Pro Pro Pro Ser Lys
35

<210> SEQ ID NO 55
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 55

His Ala Glu Gly Thr Phe Thr Ser Asp Leu Ser Lys Gln Leu Glu Glu
1               5                   10                  15
Gln Ala Ala Glu Phe Ile Val Trp Leu Val Lys Gly Arg Gly Lys Lys
            20                  25                  30
Gly Xaa Pro Pro Pro Ser Lys
        35

<210> SEQ ID NO 56
<211> LENGTH: 39
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 56

His Ala Glu Gly Thr Phe Thr Ser Asp Leu Ser Lys Gln Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 57
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 57

His Ala Glu Gly Thr Phe Thr Ser Asp Leu Ser Lys Gln Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 58
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 58

His Ala Glu Gly Thr Phe Thr Ser Asp Leu Ser Lys Gln Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 59
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 59
```

-continued

His Ala Glu Gly Thr Phe Thr Ser Asp Leu Ser Lys Gln Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 60
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 60

His Ala Glu Gly Thr Phe Thr Ser Asp Leu Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 61
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 61

His Ala Glu Gly Thr Phe Thr Ser Asp Leu Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 62
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 62

His Ala Glu Gly Thr Phe Thr Ser Asp Leu Ser Lys Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 63
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)

<223> OTHER INFORMATION: Xaa: Sar

<400> SEQUENCE: 63

His Ala Glu Gly Thr Phe Thr Ser Asp Leu Ser Lys Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 64
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 64

His Ala Glu Gly Thr Phe Thr Ser Asp Leu Ser Ser Gln Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 65
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 65

His Ala Glu Gly Thr Phe Thr Ser Asp Leu Ser Ser Gln Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 66
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 66

His Ala Glu Gly Thr Phe Thr Ser Asp Leu Ser Ser Gln Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 67
<211> LENGTH: 39
<212> TYPE: PRT
<213> ORGANISM: Artificial Sequence
<220> FEATURE:

```
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 67

His Ala Glu Gly Thr Phe Thr Ser Asp Leu Ser Ser Gln Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 68
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 68

His Ala Glu Gly Thr Phe Thr Ser Asp Leu Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 69
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 69

His Ala Glu Gly Thr Phe Thr Ser Asp Leu Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 70
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 70

His Ala Glu Gly Thr Phe Thr Ser Asp Leu Ser Ser Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 71
```

```
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 71

His Ala Glu Gly Thr Phe Thr Ser Asp Leu Ser Ser Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 72
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 72

His Lys Glu Gly Thr Phe Thr Ser Asp Val Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 73
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 73

His Lys Glu Gly Thr Phe Thr Ser Asp Val Ser Ser Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 74
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 74

His Lys Glu Gly Thr Phe Thr Ser Asp Val Ser Ser Tyr Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
```

<210> SEQ ID NO 75
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 75

His Leu Glu Gly Thr Phe Thr Ser Asp Val Ser Ser Tyr Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 76
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 76

His Leu Glu Gly Thr Phe Thr Ser Asp Val Ser Ser Tyr Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 77
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 77

His Lys Glu Gly Thr Phe Thr Ser Asp Val Ser Ser Tyr Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 78
<211> LENGTH: 39
<212> TYPE: PRT
<213> ORGANISM: Artificial Sequence

```
<220> FEATURE:
<223> OTHER INFORMATION: Synthetic Peptide

<400> SEQUENCE: 78

His Lys Glu Gly Thr Phe Thr Ser Asp Val Ser Ser Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 79
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 79

His Ile Glu Gly Thr Phe Thr Ser Asp Val Ser Ser Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 80
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 80

His Ile Glu Gly Thr Phe Thr Ser Asp Val Ser Ser Tyr Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 81
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 81

His Ile Glu Gly Thr Phe Thr Ser Asp Val Ser Ser Tyr Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35
```

```
<210> SEQ ID NO 82
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 82

His Leu Glu Gly Thr Phe Thr Ser Asp Val Ser Ser Tyr Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 83
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 83

His Xaa Glu Gly Thr Phe Thr Ser Asp Leu Ser Ser Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 84
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 84

His Lys Glu Gly Thr Phe Thr Ser Asp Val Ser Ser Tyr Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 85
<211> LENGTH: 39
<212> TYPE: PRT
```

```
<213> ORGANISM: Artificial Sequence
<220> FEATURE:
<223> OTHER INFORMATION: Synthetic Peptide

<400> SEQUENCE: 85

His Ile Glu Gly Thr Phe Thr Ser Asp Val Ser Ser Gln Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 86
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 86

His Val Glu Gly Thr Phe Thr Ser Asp Val Ser Ser Gln Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 87
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 87

His Val Glu Gly Thr Phe Thr Ser Asp Val Ser Ser Gln Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 88
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 88

His Val Glu Gly Thr Phe Thr Ser Asp Val Ser Ser Gln Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35
```

```
<210> SEQ ID NO 89
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 89

His Leu Glu Gly Thr Phe Thr Ser Asp Val Ser Ser Gln Leu Glu Xaa
 1               5                  10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 90
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 90

His Lys Glu Gly Thr Phe Thr Ser Asp Val Ser Ser Gln Leu Glu Xaa
 1               5                  10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 91
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 91

His Lys Glu Gly Thr Phe Thr Ser Asp Val Ser Ser Gln Met Glu Gly
 1               5                  10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 92
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar
```

<400> SEQUENCE: 92

His Val Glu Gly Thr Phe Thr Ser Asp Val Ser Ser Gln Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 93
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 93

His Val Glu Gly Thr Phe Thr Ser Asp Val Ser Ser Gln Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 94
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 94

His Gly Glu Gly Thr Phe Thr Ser Asp Val Ser Ser Gln Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 95
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 95

His Gly Glu Gly Thr Phe Thr Ser Asp Val Ser Ser Gln Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 96
<211> LENGTH: 39

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 96

His Ile Glu Gly Thr Phe Thr Ser Asp Val Ser Ser Gln Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 97
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 97

His Ile Glu Gly Thr Phe Thr Ser Asp Val Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 98
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 98

His Lys Glu Gly Thr Phe Thr Ser Asp Val Ser Lys Tyr Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 99
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 99

His Lys Glu Gly Thr Phe Thr Ser Asp Val Ser Lys Tyr Leu Glu Glu
1               5                   10                  15

Gln Ala Ala Glu Phe Ile Val Trp Leu Val Lys Gly Arg Gly Lys Lys
```

```
                      20                  25                  30

Gly Gly Pro Pro Pro Ser Lys
        35

<210> SEQ ID NO 100
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 100

His Ile Glu Gly Thr Phe Thr Ser Asp Val Ser Lys Tyr Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 101
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 101

His Val Glu Gly Thr Phe Thr Ser Asp Val Ser Lys Tyr Leu Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 102
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 102

His Val Glu Gly Thr Phe Thr Ser Asp Val Ser Lys Tyr Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 103
```

```
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 103

His Val Glu Gly Thr Phe Thr Ser Asp Val Ser Lys Tyr Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 104
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 104

His Ile Glu Gly Thr Phe Thr Ser Asp Val Ser Lys Tyr Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 105
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 105

His Lys Glu Gly Thr Phe Thr Ser Asp Val Ser Lys Tyr Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 106
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (34)..(34)
<223> OTHER INFORMATION: Xaa: Sar

<400> SEQUENCE: 106

His Ile Glu Gly Thr Phe Thr Ser Asp Val Ser Lys Tyr Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
```

-continued

<210> SEQ ID NO 107
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 107

His Lys Glu Gly Thr Phe Thr Ser Asp Val Ser Lys Tyr Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 108
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 108

His Val Glu Gly Thr Phe Thr Ser Asp Val Ser Lys Tyr Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 109
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 109

His Lys Glu Gly Thr Phe Thr Ser Asp Val Ser Lys Gln Leu Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 110
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE

```
<222> LOCATION: (34)..(34)
<223> OTHER INFORMATION: Xaa: Sar

<400> SEQUENCE: 110

His Ile Glu Gly Thr Phe Thr Ser Asp Val Ser Lys Gln Leu Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 111
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 111

His Lys Glu Gly Thr Phe Thr Ser Asp Val Ser Lys Gln Leu Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 112
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 112

His Xaa Glu Gly Thr Phe Thr Ser Asp Val Ser Lys Gln Leu Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 113
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 113

His Lys Glu Gly Thr Phe Thr Ser Asp Val Ser Lys Gln Leu Glu Xaa
1               5                   10                  15

Gln Ala Ala Glu Phe Ile Val Trp Leu Val Lys Gly Arg Gly Lys Lys
            20                  25                  30
```

```
Gly Gly Pro Pro Pro Ser Lys
        35

<210> SEQ ID NO 114
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 114

His Xaa Glu Gly Thr Phe Thr Ser Asp Val Ser Lys Gln Leu Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 115
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 115

His Ile Glu Gly Thr Phe Thr Ser Asp Val Ser Lys Gln Met Glu Gly
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 116
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 116

His Xaa Glu Gly Thr Phe Thr Ser Asp Val Ser Lys Gln Met Glu Gly
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35
```

<210> SEQ ID NO 117
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 117

His Gly Glu Gly Thr Phe Thr Ser Asp Val Ser Lys Gln Met Glu Glu
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 118
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 118

His Xaa Glu Gly Thr Phe Thr Ser Asp Val Ser Lys Gln Met Glu Glu
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 119
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 119

His Lys Glu Gly Thr Phe Thr Ser Asp Val Ser Lys Gln Met Glu Xaa
1               5                   10                  15

Gln Ala Ala Glu Phe Ile Val Trp Leu Val Lys Gly Arg Gly Lys Lys
            20                  25                  30

Gly Gly Pro Pro Pro Ser Lys
        35

<210> SEQ ID NO 120
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib

```
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (34)..(34)
<223> OTHER INFORMATION: Xaa: Sar

<400> SEQUENCE: 120

His Xaa Glu Gly Thr Phe Thr Ser Asp Val Ser Lys Gln Met Glu Xaa
1               5                   10                  15

Gln Ala Ala Glu Phe Ile Val Trp Leu Val Lys Gly Arg Gly Lys Lys
            20                  25                  30

Gly Xaa Pro Pro Pro Ser Lys
        35

<210> SEQ ID NO 121
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 121

His Ala Glu Gly Thr Phe Thr Ser Asp Val Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 122
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 122

His Ala Glu Gly Thr Phe Thr Ser Asp Val Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 123
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 123

His Ala Glu Gly Thr Phe Thr Ser Asp Val Ser Ser Tyr Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40
```

```
<210> SEQ ID NO 124
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 124

His Ala Glu Gly Thr Phe Thr Ser Asp Val Ser Ser Tyr Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 125
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 125

His Ala Glu Gly Thr Phe Thr Ser Asp Val Ser Ser Tyr Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 126
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 126

His Ala Glu Gly Thr Phe Thr Ser Asp Val Ser Ser Tyr Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 127
<211> LENGTH: 40
<212> TYPE: PRT
<213> ORGANISM: Artificial Sequence
<220> FEATURE:
```

<223> OTHER INFORMATION: Synthetic Peptide

<400> SEQUENCE: 127

His Ala Glu Gly Thr Phe Thr Ser Asp Val Ser Ser Tyr Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 128
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 128

His Ala Glu Gly Thr Phe Thr Ser Asp Val Ser Ser Tyr Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 129
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 129

His Ala Glu Gly Thr Phe Thr Ser Asp Val Ser Ser Tyr Met Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 130
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 130

His Ala Glu Gly Thr Phe Thr Ser Asp Val Ser Ser Tyr Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 131

```
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 131

His Ala Glu Gly Thr Phe Thr Ser Asp Val Ser Ser Tyr Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 132
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 132

His Ala Glu Gly Thr Phe Thr Ser Asp Val Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 133
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 133

His Ala Glu Gly Thr Phe Thr Ser Asp Val Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 134
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 134

His Ala Glu Gly Thr Phe Thr Ser Asp Val Ser Ser Gln Leu Glu Glu
1               5                   10                  15
```

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 135
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 135

His Ala Glu Gly Thr Phe Thr Ser Asp Val Ser Ser Gln Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 136
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 136

His Ala Glu Gly Thr Phe Thr Ser Asp Val Ser Ser Gln Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 137
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 137

His Ala Glu Gly Thr Phe Thr Ser Asp Val Ser Ser Gln Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

```
<210> SEQ ID NO 138
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 138

His Ala Glu Gly Thr Phe Thr Ser Asp Val Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 139
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 139

His Ala Glu Gly Thr Phe Thr Ser Asp Val Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 140
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 140

His Ala Glu Gly Thr Phe Thr Ser Asp Val Ser Ser Gln Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 141
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 141

His Ala Glu Gly Thr Phe Thr Ser Asp Val Ser Ser Gln Met Glu Glu
1               5                   10                  15

Gln Ala Ala Lys Glu Phe Ile Val Trp Leu Val Lys Gly Arg Gly Lys
            20                  25                  30
```

```
Lys Gly Xaa Pro Pro Pro Ser Lys
        35                  40

<210> SEQ ID NO 142
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 142

His Ala Glu Gly Thr Phe Thr Ser Asp Val Ser Ser Gln Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 143
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 143

His Ala Glu Gly Thr Phe Thr Ser Asp Val Ser Ser Gln Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 144
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 144

His Ala Glu Gly Thr Phe Thr Ser Asp Val Ser Lys Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 145
<211> LENGTH: 40
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (35)..(35)
<223> OTHER INFORMATION: Xaa: Sar

<400> SEQUENCE: 145

His Ala Glu Gly Thr Phe Thr Ser Asp Val Ser Lys Tyr Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 146
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 146

His Ala Glu Gly Thr Phe Thr Ser Asp Val Ser Lys Tyr Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 147
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 147

His Ala Glu Gly Thr Phe Thr Ser Asp Val Ser Lys Tyr Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 148
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 148

His Ala Glu Gly Thr Phe Thr Ser Asp Val Ser Lys Tyr Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40
```

```
<210> SEQ ID NO 149
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 149

His Ala Glu Gly Thr Phe Thr Ser Asp Val Ser Lys Tyr Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 150
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 150

His Ala Glu Gly Thr Phe Thr Ser Asp Val Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 151
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 151

His Ala Glu Gly Thr Phe Thr Ser Asp Val Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 152
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 152

His Ala Glu Gly Thr Phe Thr Ser Asp Val Ser Lys Tyr Met Glu Glu
```

```
                1               5                   10                  15
Gln Ala Ala Lys Glu Phe Ile Val Trp Leu Val Lys Gly Arg Gly Lys
                20                  25                  30

Lys Gly Gly Pro Pro Pro Ser Lys
        35                  40

<210> SEQ ID NO 153
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 153

His Ala Glu Gly Thr Phe Thr Ser Asp Val Ser Lys Tyr Met Glu Glu
1               5                   10                  15

Gln Ala Ala Lys Glu Phe Ile Val Trp Leu Val Lys Gly Arg Gly Lys
                20                  25                  30

Lys Gly Xaa Pro Pro Pro Ser Lys
        35                  40

<210> SEQ ID NO 154
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 154

His Ala Glu Gly Thr Phe Thr Ser Asp Val Ser Lys Tyr Met Glu Xaa
1               5                   10                  15

Gln Ala Ala Lys Glu Phe Ile Val Trp Leu Val Lys Gly Arg Gly Lys
                20                  25                  30

Lys Gly Gly Pro Pro Pro Ser Lys
        35                  40

<210> SEQ ID NO 155
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 155

His Ala Glu Gly Thr Phe Thr Ser Asp Val Ser Lys Tyr Met Glu Xaa
1               5                   10                  15

Gln Ala Ala Lys Glu Phe Ile Val Trp Leu Val Lys Gly Arg Gly Lys
                20                  25                  30

Lys Gly Xaa Pro Pro Pro Ser Lys
        35                  40
```

<210> SEQ ID NO 156
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 156

His Ala Glu Gly Thr Phe Thr Ser Asp Val Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 157
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 157

His Ala Glu Gly Thr Phe Thr Ser Asp Val Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 158
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 158

His Ala Glu Gly Thr Phe Thr Ser Asp Val Ser Lys Gln Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 159
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 159

His Ala Glu Gly Thr Phe Thr Ser Asp Val Ser Lys Gln Leu Glu Glu
1               5                   10                  15

Gln Ala Ala Lys Glu Phe Ile Val Trp Leu Val Lys Gly Arg Gly Lys

```
              20                  25                  30

Lys Gly Xaa Pro Pro Pro Ser Lys
        35                  40

<210> SEQ ID NO 160
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 160

His Ala Glu Gly Thr Phe Thr Ser Asp Val Ser Lys Gln Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 161
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 161

His Ala Glu Gly Thr Phe Thr Ser Asp Val Ser Lys Gln Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 162
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 162

His Ala Glu Gly Thr Phe Thr Ser Asp Val Ser Lys Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 163
<211> LENGTH: 40
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 163

His Ala Glu Gly Thr Phe Thr Ser Asp Val Ser Lys Gln Met Glu Gly
 1               5                  10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 164
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 164

His Ala Glu Gly Thr Phe Thr Ser Asp Val Ser Lys Gln Met Glu Glu
 1               5                  10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 165
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 165

His Ala Glu Gly Thr Phe Thr Ser Asp Val Ser Lys Gln Met Glu Glu
 1               5                  10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 166
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 166

His Ala Glu Gly Thr Phe Thr Ser Asp Val Ser Lys Gln Met Glu Xaa
 1               5                  10                  15

Gln Ala Ala Lys Glu Phe Ile Val Trp Leu Val Lys Gly Arg Gly Lys
            20                  25                  30

Lys Gly Gly Pro Pro Pro Ser Lys
```

35                  40

<210> SEQ ID NO 167
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 167

His Ala Glu Gly Thr Phe Thr Ser Asp Val Ser Lys Gln Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 168
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 168

His Ala Glu Gly Thr Phe Thr Ser Asp Leu Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 169
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 169

His Ala Glu Gly Thr Phe Thr Ser Asp Leu Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 170
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 170

His Ala Glu Gly Thr Phe Thr Ser Asp Leu Ser Lys Gln Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 171
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 171

His Ala Glu Gly Thr Phe Thr Ser Asp Leu Ser Lys Gln Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 172
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 172

His Ala Glu Gly Thr Phe Thr Ser Asp Leu Ser Lys Gln Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 173
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 173

His Ala Glu Gly Thr Phe Thr Ser Asp Leu Ser Lys Gln Leu Glu Xaa
1               5                   10                  15

Gln Ala Ala Lys Glu Phe Ile Val Trp Leu Val Lys Gly Arg Gly Lys
            20                  25                  30

```
Lys Gly Xaa Pro Pro Pro Ser Lys
        35                  40

<210> SEQ ID NO 174
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 174

His Ala Glu Gly Thr Phe Thr Ser Asp Leu Ser Lys Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 175
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 175

His Ala Glu Gly Thr Phe Thr Ser Asp Leu Ser Lys Gln Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 176
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 176

His Ala Glu Gly Thr Phe Thr Ser Asp Leu Ser Lys Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 177
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 177

His Ala Glu Gly Thr Phe Thr Ser Asp Leu Ser Lys Tyr Leu Glu Gly
1               5                   10                  15
```

```
Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 178
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 178

His Ala Glu Gly Thr Phe Thr Ser Asp Leu Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 179
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 179

His Ala Glu Gly Thr Phe Thr Ser Asp Leu Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 180
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 180

His Ala Glu Gly Thr Phe Thr Ser Asp Leu Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 181
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar
```

<400> SEQUENCE: 181

His Ala Glu Gly Thr Phe Thr Ser Asp Leu Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 182
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 182

His Ala Glu Gly Thr Phe Thr Ser Asp Leu Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 183
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 183

His Ala Glu Gly Thr Phe Thr Ser Asp Leu Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 184
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 184

His Ala Glu Gly Thr Phe Thr Ser Asp Leu Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 185
<211> LENGTH: 40
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MISC_FEATURE
<222> LOCATION: (35)..(35)
<223> OTHER INFORMATION: Xaa: Sar

<400> SEQUENCE: 185
```

His Ala Glu Gly Thr Phe Thr Ser Asp Leu Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

```
<210> SEQ ID NO 186
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 186
```

His Ala Glu Gly Thr Phe Thr Ser Asp Leu Ser Ser Tyr Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

```
<210> SEQ ID NO 187
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 187
```

His Ala Glu Gly Thr Phe Thr Ser Asp Leu Ser Ser Tyr Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

```
<210> SEQ ID NO 188
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 188
```

His Lys Glu Gly Thr Phe Thr Ser Asp Val Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

```
<210> SEQ ID NO 189
<211> LENGTH: 40
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 189
```

His Lys Glu Gly Thr Phe Thr Ser Asp Val Ser Ser Tyr Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

```
<210> SEQ ID NO 190
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 190
```

His Lys Glu Gly Thr Phe Thr Ser Asp Val Ser Ser Tyr Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

```
<210> SEQ ID NO 191
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 191
```

His Leu Glu Gly Thr Phe Thr Ser Asp Val Ser Ser Tyr Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

```
<210> SEQ ID NO 192
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 192
```

His Leu Glu Gly Thr Phe Thr Ser Asp Val Ser Ser Tyr Leu Glu Xaa
1               5                   10                  15

Gln Ala Ala Lys Glu Phe Ile Val Trp Leu Val Lys Gly Arg Gly Lys
            20                  25                  30

```
<210> SEQ ID NO 193
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 193

His Lys Glu Gly Thr Phe Thr Ser Asp Val Ser Ser Tyr Leu Glu Xaa
1               5                  10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 194
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 194

His Lys Glu Gly Thr Phe Thr Ser Asp Val Ser Ser Tyr Met Glu Gly
1               5                  10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 195
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 195

His Ile Glu Gly Thr Phe Thr Ser Asp Val Ser Ser Tyr Met Glu Gly
1               5                  10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 196
<211> LENGTH: 40
<212> TYPE: PRT
<213> ORGANISM: Artificial Sequence
<220> FEATURE:
<223> OTHER INFORMATION: Synthetic Peptide
```

Preceding continuation:

```
Lys Gly Gly Pro Pro Pro Ser Lys
        35                  40
```

```
<400> SEQUENCE: 196

His Ile Glu Gly Thr Phe Thr Ser Asp Val Ser Ser Tyr Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 197
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 197

His Ile Glu Gly Thr Phe Thr Ser Asp Val Ser Ser Tyr Met Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 198
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 198

His Leu Glu Gly Thr Phe Thr Ser Asp Val Ser Ser Tyr Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 199
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 199

His Xaa Glu Gly Thr Phe Thr Ser Asp Leu Ser Ser Tyr Met Glu Gly
1               5                   10                  15

Gln Ala Ala Lys Glu Phe Ile Val Trp Leu Val Lys Gly Arg Gly Lys
```

```
Lys Gly Xaa Pro Pro Pro Ser Lys
        35                  40

<210> SEQ ID NO 200
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 200

His Lys Glu Gly Thr Phe Thr Ser Asp Val Ser Ser Tyr Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 201
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 201

His Ile Glu Gly Thr Phe Thr Ser Asp Val Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 202
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 202

His Val Glu Gly Thr Phe Thr Ser Asp Val Ser Ser Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 203
<211> LENGTH: 40
<212> TYPE: PRT
<213> ORGANISM: Artificial Sequence
<220> FEATURE:
```

```
<223> OTHER INFORMATION: Synthetic Peptide

<400> SEQUENCE: 203

His Val Glu Gly Thr Phe Thr Ser Asp Val Ser Ser Gln Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 204
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 204

His Val Glu Gly Thr Phe Thr Ser Asp Val Ser Ser Gln Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 205
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 205

His Leu Glu Gly Thr Phe Thr Ser Asp Val Ser Ser Gln Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 206
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 206

His Lys Glu Gly Thr Phe Thr Ser Asp Val Ser Ser Gln Leu Glu Xaa
1               5                   10                  15
```

```
Gln Ala Ala Lys Glu Phe Ile Val Trp Leu Val Lys Gly Arg Gly Lys
            20                  25                  30

Lys Gly Xaa Pro Pro Pro Ser Lys
        35                  40
```

<210> SEQ ID NO 207
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 207

```
His Lys Glu Gly Thr Phe Thr Ser Asp Val Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40
```

<210> SEQ ID NO 208
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 208

```
His Val Glu Gly Thr Phe Thr Ser Asp Val Ser Ser Gln Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40
```

<210> SEQ ID NO 209
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 209

```
His Val Glu Gly Thr Phe Thr Ser Asp Val Ser Ser Gln Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40
```

<210> SEQ ID NO 210
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 210

His Gly Glu Gly Thr Phe Thr Ser Asp Val Ser Ser Gln Met Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 211
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 211

His Gly Glu Gly Thr Phe Thr Ser Asp Val Ser Ser Gln Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 212
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 212

His Ile Glu Gly Thr Phe Thr Ser Asp Val Ser Ser Gln Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 213
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 213

His Ile Glu Gly Thr Phe Thr Ser Asp Val Ser Lys Tyr Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

```
<210> SEQ ID NO 214
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 214

His Lys Glu Gly Thr Phe Thr Ser Asp Val Ser Lys Tyr Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 215
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 215

His Lys Glu Gly Thr Phe Thr Ser Asp Val Ser Lys Tyr Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 216
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 216

His Ile Glu Gly Thr Phe Thr Ser Asp Val Ser Lys Tyr Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 217
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 217

His Val Glu Gly Thr Phe Thr Ser Asp Val Ser Lys Tyr Leu Glu Xaa
1               5                   10                  15
```

```
Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 218
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 218

His Val Glu Gly Thr Phe Thr Ser Asp Val Ser Lys Tyr Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 219
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 219

His Val Glu Gly Thr Phe Thr Ser Asp Val Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 220
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 220

His Ile Glu Gly Thr Phe Thr Ser Asp Val Ser Lys Tyr Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 221
<211> LENGTH: 40
<212> TYPE: PRT
```

```
<213> ORGANISM: Artificial Sequence
<220> FEATURE:
<223> OTHER INFORMATION: Synthetic Peptide

<400> SEQUENCE: 221

His Lys Glu Gly Thr Phe Thr Ser Asp Val Ser Lys Tyr Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 222
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 222

His Ile Glu Gly Thr Phe Thr Ser Asp Val Ser Lys Tyr Met Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 223
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 223

His Lys Glu Gly Thr Phe Thr Ser Asp Val Ser Lys Tyr Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 224
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 224

His Val Glu Gly Thr Phe Thr Ser Asp Val Ser Lys Tyr Met Glu Xaa
```

```
                1               5                  10                 15
Gln Ala Ala Lys Glu Phe Ile Val Trp Leu Val Lys Gly Arg Gly Lys
            20                  25                 30

Lys Gly Xaa Pro Pro Pro Ser Lys
        35                  40

<210> SEQ ID NO 225
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 225

His Lys Glu Gly Thr Phe Thr Ser Asp Val Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 226
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (35)..(35)
<223> OTHER INFORMATION: Xaa: Sar

<400> SEQUENCE: 226

His Ile Glu Gly Thr Phe Thr Ser Asp Val Ser Lys Gln Leu Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 227
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 227

His Lys Glu Gly Thr Phe Thr Ser Asp Val Ser Lys Gln Leu Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 228
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
```

```
<220> FEATURE:
<221> NAME/KEY: MISC_FEATURE
<222> LOCATION: (35)..(35)
<223> OTHER INFORMATION: Xaa: Sar

<400> SEQUENCE: 228

His Xaa Glu Gly Thr Phe Thr Ser Asp Val Ser Lys Gln Leu Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 229
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 229

His Lys Glu Gly Thr Phe Thr Ser Asp Val Ser Lys Gln Leu Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 230
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 230

His Xaa Glu Gly Thr Phe Thr Ser Asp Val Ser Lys Gln Leu Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 231
<211> LENGTH: 40
<212> TYPE: PRT
<213> ORGANISM: Artificial Sequence
<220> FEATURE:
<223> OTHER INFORMATION: Synthetic Peptide
```

```
<400> SEQUENCE: 231

His Ile Glu Gly Thr Phe Thr Ser Asp Val Ser Lys Gln Met Glu Gly
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 232
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 232

His Xaa Glu Gly Thr Phe Thr Ser Asp Val Ser Lys Gln Met Glu Gly
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 233
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 233

His Gly Glu Gly Thr Phe Thr Ser Asp Val Ser Lys Gln Met Glu Glu
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 234
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar
```

<400> SEQUENCE: 234

His Xaa Glu Gly Thr Phe Thr Ser Asp Val Ser Lys Gln Met Glu Glu
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 235
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (16)..(16)
<223> OTHER INFORMATION: Xaa: Aib

<400> SEQUENCE: 235

His Lys Glu Gly Thr Phe Thr Ser Asp Val Ser Lys Gln Met Glu Xaa
1               5                   10                  15

Gln Ala Ala Lys Glu Phe Ile Val Trp Leu Val Lys Gly Arg Gly Lys
            20                  25                  30

Lys Gly Gly Pro Pro Pro Ser Lys
        35                  40

<210> SEQ ID NO 236
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: Aib
<220> FEATURE:
<221> NAME/KEY: MISC_FEATURE
<222> LOCATION: (16)..(16)
<223> OTHER INFORMATION: Xaa: Aib
<220> FEATURE:
<221> NAME/KEY: MISC_FEATURE
<222> LOCATION: (35)..(35)
<223> OTHER INFORMATION: Xaa: Sar

<400> SEQUENCE: 236

His Xaa Glu Gly Thr Phe Thr Ser Asp Val Ser Lys Gln Met Glu Xaa
1               5                   10                  15

Gln Ala Ala Lys Glu Phe Ile Val Trp Leu Val Lys Gly Arg Gly Lys
            20                  25                  30

Lys Gly Xaa Pro Pro Pro Ser Lys
        35                  40

<210> SEQ ID NO 237
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa: D-Ala
<220> FEATURE:
<221> NAME/KEY: MISC_FEATURE
<222> LOCATION: (14)..(14)
<223> OTHER INFORMATION: Xaa: Nle -continued

```
<400> SEQUENCE: 237

His Xaa Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
                20                  25                  30

Ser Gly Ala Pro Pro Pro Ser Lys
            35                  40

<210> SEQ ID NO 238
<211> LENGTH: 67
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: Any natural or non-natural amino acid
<220> FEATURE:
<221> NAME/KEY: MISC_FEATURE
<222> LOCATION: (10)..(10)
<223> OTHER INFORMATION: Any natural or non-natural amino acid
<220> FEATURE:
<221> NAME/KEY: MISC_FEATURE
<222> LOCATION: (12)..(14)
<223> OTHER INFORMATION: Any natural or non-natural amino acid
<220> FEATURE:
<221> NAME/KEY: MISC_FEATURE
<222> LOCATION: (16)..(17)
<223> OTHER INFORMATION: Any natural or non-natural amino acid
<220> FEATURE:
<221> NAME/KEY: MISC_FEATURE
<222> LOCATION: (19)..(21)
<223> OTHER INFORMATION: Any natural or non-natural amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Any natural or non-natural amino acid
<220> FEATURE:
<221> NAME/KEY: MISC_FEATURE
<222> LOCATION: (27)..(39)
<223> OTHER INFORMATION: Any natural or non-natural amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (52)..(64)
<223> OTHER INFORMATION: Xaa can be any naturally occurring amino acid

<400> SEQUENCE: 238

Xaa Xaa Gly Leu Gly Leu Tyr Thr His Arg Pro His Glu Thr His Arg
1               5                   10                  15

Ser Glu Arg Ala Ser Pro Xaa Ser Glu Arg Xaa Xaa Xaa Gly Leu Xaa
                20                  25                  30

Xaa Ala Leu Ala Xaa Xaa Xaa Pro His Glu Ile Leu Glu Xaa Thr Arg
            35                  40                  45

Pro Leu Glu Xaa Xaa Xaa Xaa Xaa Xaa Xaa Xaa Xaa Xaa Xaa Xaa Xaa
        50                  55                  60

Leu Tyr Ser
65
```

GLP-1 ANALOGUES AND THEIR PHARMACEUTICAL SALTS AND USES

REFERENCE TO EARLIER FILED APPLICATIONS

This application is a continuation of U.S. patent application Ser. No. 13/388,056, filed Jan. 30, 2012, which is a 371 national phase of PCT/CN2010/075548, filed Jul. 29, 2010, and claims the benefit of Chinese Application No. 200910165559.9, filed Jul. 30, 2009, the disclosures of which are incorporated, in their entirety, by this reference.

FIELD OF THE INVENTION

This invention relates to analogues of the human Glucagon-like peptide-1 (GLP-1) and pharmaceutical salts thereof. The GLP-1 analogues provided in this invention have the function of the human GLP-1 peptide and a longer half-life in vivo compared with the native protein. The present invention also relates to the use of GLP-1 analogues, the pharmaceutical salts thereof, or use as a pharmaceutical composition thereof in the treatment of non-insulin-dependent diabetes, insulin-dependent diabetes and obesity.

BACKGROUND OF THE INVENTION

Diabetes mellitus is a global epidemic disease and is a metabolic disorder relating to glucose, protein and lipids due to the absolute or relative deficiency of insulin (See Chen Ruijie. Status of research on diabetes drugs. Academic journal of Guangdong College of Pharmacy, 2001, 7(2):131-133). Diabetes mellitus can be divided into type I diabetes mellitus and type II diabetes mellitus (Type 2 diabetes mellitus, T2DM, the same below) according to the pathogenesis thereof 90-95% of all the patients diagnosed with diabetes mellitus suffer from T2DM, and patients are often afflicted with obesity, a deficiency of physical activity. T2DM is most common in the aging population, or among those with family history of diabetes mellitus T2DM. It is also a progressive disease. According to statistical data in 2000, the World Health Organization estimated that there are about 171 million people worldwidely who suffer from diabetes mellitus. In 2005, the U.S. Centers for Disease Control and Prevention. estimated that 20.8 million Americans suffer from diabetes mellitus which is about 7% of the population of the United States. In 2006, the International Diabetes Federation, estimated that the global number of patients suffering from diabetes mellitus is about 246 million (about 5.9% of the totally global population) and indicated that 46% of the patients were 40-59 years old.

T2DM is characterized by the inhibition of the secration of insulin and pancreatic β-cell dysfunction which results in insulin deficiency and hyperglycemia. (See Ferrannini E. Insulin resistance versus insulin deficiency in non-insulin-dependent diabetes mellitus: problems and prospects. Endocr Rev. 1998, 19(4):477-490). T2DM patients typically suffer from a postprandial and fasting hyperglycemia (fasting glucose >125 mg/dL). Observed high blood sugar is the result of pancreatic β-cells failure to secrete enough insulin in the surrounding tissue. (See Weyer C., Bogardus C., Mott D M., et al. The natural history of insulin secretory dysfunction and insulin resistance in the pathogenesis of type 2 diabetes mellitus. J. Clin. Invest. 1999, 104(6): 787-794).

A major risk factor of T2DM is obesity, which is itself very harmful to human health. T2DM often co-exists with other high-risk diseases such as hypertension and dyslipidemia. 60% of T2DM patients are accompanied by microvascular complications, including retinopathy and neuropathy, and also are accompanied by cardiovascular morbidities, such as coronary heart disease, myocardial infarction, shock, and the like. In the U.S., cardiovascular diseases (CVD) is the major cause resulting in mortality, and T2DM is the major risk factor causing macrovascular complications such as an atherosclerosis, myocardial infarction, shock, and peripheral vascular diseases. The risk of death caused by heart diseases with diabetes is 2-4 times higher than that of a non-diabetes person. In addition, nearly 65% of people with diabetes die of heart disease.

In addition to the physical and physiological harm to patients, T2DM causes great economic burden on society. According to statistics, the cost of the treatment of complications associated with diabetes is about $ 22.9 billion; the total cost of the treatment of T2DM and complications thereof is nearly $ 57.1 billion every year in the U.S.

Drugs for the treatment of T2DM have been sought. These include the early oral hypoglycemic drugs of sulfonyl class and biguanide class and the recent insulin sensitizer and α-glucosidase inhibitors, the development of animal insulins and human insulins in a variety of new regimes and formulations, the research of new mechanisms of drug treatment by simply increasing insulin, and new ways acting on the insulin-producing cells. Weight gain is a common side-effect after the administration of oral or injection hypoglycemic agents, which may reduce compliance, and may increase the risk of developing cardiovascular disease. Therefore, developing new types of drugs for the treatment of T2DM which have high safety profiles, good patient compliance and low side-effects is desirable.

As early as 100 years ago, Moore proposed that the duodenum can secrete a "chemical stimulant" stimulating pancreatic secretion. Attempts to inject gut-extract to treat diabetes were undertaken. Subsequently it was discovered that humoral factors derived from intestinal secretion can enhance the function of the pancreas endocrine, and about 50% of insulin secretion induced by intravenous or oral glucose is derived from the stimulus of peptides produced in the gut. Therefore Zunz and Labarre described the concept of "incretin." Two kinds of incretins have been isolated so far, namely glucose-dependent insulinotropic polypeptide (GIP) and glucagon-like peptide-1 (GLP-1). Both GIP and GLP-1 are secreted by specific intestinal nerve cells when a related nutrient is absorbed. GIP is secreted by the duodenum and proximal jejunal K cells. GLP-1 is synthesized in L cells and mainly exists in the distal small bowel and colon (See Drucker D J. Enhancing incretin action for the treatment of type 2 diabetes. Diabetes Care. 2003, 26(10):2929-2940).

GLP-1 exists in two bio-active forms in blood plasma, namely GLP-1 (7-37) and GLP-1 (7-36). The difference between the two forms resides in one amino acid residue, and their biological effects and in vivo half-life are the same. (See Drucker D J. Enhancing incretin action for the treatment of type 2 diabetes. Diabetes Care. 2003, 26(10):2929-2940).

GLP-1 is usually referred to as GLP-1 (7-37) and GLP-1 (7-36) amide. GIP and GLP-1 are degraded to inactive forms by dipeptidyl peptidase-IV (DPP-IV) quickly after released in the gastrointestinal tract, so that the in vivo half-life of GIP and GLP-1 is very short (in vivo half-life of GIP is about 5-7 minutes, in vivo half-life of GLP-1 is about 2 minutes). (See Drucker D J. Enhancing incretin action for the treatment of type 2 diabetes. Diabetes Care. 2003, 26(10):2929-2940). Researches show that most of the degradation process occurs when the GIP and GLP-1 enter into the blood vessels containing DPP-IV, and a small amount of GLP-1 and GIP which has not been degraded will enter into the pancreas and associate with binding sites to stimulate insulin release from β-cells. Different from the mechanism of sulfonylurea to directly promote functional β-cells to release insulin, most of the effects of incretin are glucose-dependent. In addition, some in vitro tests on animals and humans have shown that GLP-1 also functions to suppress α-cell and reduce glucagon hypersecretion.

Although plasma GIP levels in patients with T2DM are normal, when the function of incretin declines significantly, the GLP-1 levels in patients with T2DM decline. Thus, drugs based on GLP-1 contribute more to treatment of T2DM. Although the levels of both GLP-1 (7-37) and GLP-1 (7-36) amide will increase in several minutes after a meal, and the content of GLP-1 (7-36) amide is more, so the GLP-1 secretion might have been greatly increased by the double effect of endocrine and transmission of neural signal before the digested food enters the small intestine and colon. The plasma level of GLP-1 under a fasting state is very low (about 5-10 pmol/L), and is increased rapidly after eating (up to 15-50 pmol/L). Under the double function of DPP-IV and renal clearance, the level in vivo of GLP-1 in circulation is decreased rapidly. Other enzymes such as human neutral endopeptidase 24•11 may also play a vital role in inactivating clearacne of GLP-1. Because the second amino acid residue of GLP-1 is alanine, which is a good substrate of DPP-IV, GLP-1 is easily degraded into inactive peptide fragments. In fact, the DPP-IV in vivo is postulated as the key reason for loss of the activity of the incretin. Experiments show that GLP-1 levels in mice, in which DPP-IV gene has been silenced, is higher than in normal mice. Significantly, insulin secretion is increased, too. Just because the presence of DPP-IV, the content in vivo (except in plasma) of the nondegradaded and biologically active GLP-1 is only 10-20% of the total content of GLP-1 in plasma. (See Deacon C F, Nauck M A, Toft-Nielsen M, et al. Both subcutaneously and intravenously administered, glucagon-like peptide 1 is rapidly degraded from the $NH_2$-terminus in type 2-diabetic patients and in healthy subjects. (See Diabetes. 1995, 44(9): 1126-1131).

GLP-1 and GIP play their respective roles through binding to different G-protein-coupled receptors (GPCRs). Most of GIP receptors are expressed by pancreatic β-cells, and a minor part of GIP receptors are expressed by adipose tissue and the central nervous system. In contrast, GLP-1 receptors are mainly expressed in the pancreatic α- and β-cells and peripheral tissues including the central and peripheral nervous systems, brain, kidney, lung and gastrointestinal tract and the like. The activation of two incretins in β-cells will result in the rapid increase of the level of cAMP and intracellular calcium, thereby rleading to their extracellular secretion in a glucose-dependent manner. The sustained signal transmission from incretin receptors is associated with protein kinase A, resulting in gene transcription, increasing insulin biosynthesis and stimulating β-cell proliferation. (See Gallwitz B. Glucagon-like peptide-1-based therapies for the treatment of type 2 diabetes mellitus. Treat Endocrinol. 2005, 4(6):361-370). The activation of GLP-1 receptor and GIP receptor can also inhibit the apoptosis of pancreatic β-cells of rodent and human, while increasing their survival (See Li Y, Hansotia T, Yusta B, et al. Glucagon-like peptide-1 receptor signaling modulates beta cell apoptosis. J Biol Chem. 2003, 278(1): 471-478). Consistent with the expression of GLP-1 receptor, GLP-1 can also inhibit glucagon secretion, gastric emptying and food intake, and enhance the degradation of glucose through the neural mechanism. It shall be noted that, as with other insulin secretion mechanisms, the role of GLP-1 to control the level of glucose is glucagon-dependent and the counter-regulatory release of glucagon caused by low blood sugar is fully retained even at the pharmacological level of GLP-1.

The important physiological role of endogenous GLP-1 and GIP in glucose homeostasis has been studied in-depth through using receptor antagonists or gene knockout mice. Acute antagonism of GLP-1 or GIP reduces insulin secretion in vivo of rodents and increases plasma glucose content. Similarly, the mutant mice, in which GIP or GLP-1 receptor is inactivated, also experience defective glucose-stimulated insulin secretion and damaged glucose tolerance. GLP-1 also has a function of regulating fasting blood glucose, because the acute antagonists or damage on the GLP-1 gene will cause the increase of fasting glucose level of rodents. At the same time, GLP-1 is the basis of glucose control in human bodies, and studies on the antagonist of Exendin (9-39) have shown that the destruction of GLP-1 function will result in defective glucose-stimulated insulin secretion, decreased glucose clearance rate, increased glucagon levels and accelerated gastric emptying. The physiological roles of GLP-1 (see Deacon C F. Therapeutic strategies based on glucagon-like peptide 1. Diabetes. 2004, 53(9):2181-2189) comprise: (1) helping to organize glucose absorption, mediate glucose-dependent insulin secretion; (2) inhibiting postprandial glucagon secretion, reducing hepatic glucose release; (3) regulating gastric emptying, preventing excessive circulating of glucose when the food is absorbed in the intestine; and (4) inhibiting food intake (such as appetite). Also, animal studies also showed a physiological role for stabilizing the number of pancreatic β-cells in vivo.

Due to the beneficial effects of GLP-1 and GIP in controlling blood sugar and many other aspects, especially their characteristics of not producing hypoglycemia and delaying gastric emptying to control weight, the compounds attract the interest of many scientists. Further studies of based on GLP-1 and GIP for the treatment of T2DM have been pursued. It is well known that T2DM patients lack or lose the incretin effect. One reason is that incretin effect of GIP in vivo in the T2DM patient is significantly reduced. Meanwhile, the level of GLP-1 in vivo in T2DM patients is very low, and the level of GLP-1 caused by dietary stimuli is significantly reduced. (See Toft-Nielsen M B, Damholt M B, Madsbad S, et al. Determinants of the impaired secretion of glucagon-like peptide-1 in type 2 diabetic patients. J Clin Endocrinol Metab. 2001, 86(8):3717-3723). Because the role of GLP-1 in vivo in patients with T2DM has been partially reserved, GLP-1 synergist is one of the research directions of the drugs designed to enhance the incretin effect in T2DM patients.

GLP-1 analogues, may act similarly to endogenous GLP, by inhibiting the release of glucagon and stimulate insulin secretion both in vivo in a glucose-dependent manner and thus its role for lowering blood glucose exhibit a self-limitation, which generally does not cause hypoglycemia in large doses. Some literature reports that GLP-1 can reduce blood sugar to a level below normal, and this effect is transient and considered a natural result of GLP-1 promoted insulin secretion. GLP-1 can temporarily reduce blood sugar to a level below normal level but does not cause serious and persistent hypoglycemia. Besides directly reducing blood glucose, GLP-1 can also reduce the quantity of food intake, which has been verified in rodents and humans. The level of blood glucose, therefore, can be controlled by reducing body weight indirectly. GLP-1 also has the potential role of inhibiting the secretion of gastrin and gastric acid stimulated by eating, and these functions show that GLP-1 may also have a role in the prevention of peptic ulcer. Mechanisms of action for GLP-1 make it an ideal drug for the treatment of patients with type 2 diabetes, but also the drug for the treatment of patients with obesity diabetes. GLP-1 can enhance the satiety of the patients, reduce food intake and maintain body weight or lose weight. Several studies suggest that GLP-1 can prevent the conversion from impaired glucose tolerance to diabetes, and some literature reports that the GLP-1 class of compounds has direct effect on the growth and proliferation of pancreatic β-cells in experimental animals. It was found by some experiments that GLP-1 can promote the differentiation from pancreatic stem cells to functional β-cells. These results suggest that GLP-1 has the function of protecting pancreatic islet and delaying the progression of diabetes, and can maintain the morphologies and functions of β-cells, while reduce the apoptosis of β-cells. Because some oral drugs and exogenous insulins can not inhibit or reduce the exorbitant glucagon secretion in patients with T2DM, GLP-1 analogues can affect glucagon hypersecretion through directly inhibiting glucagon release or inhibition of glucagon resulted from promoting insulin secretion. The postprandial hyperglycemia can be reduced effectively through these two mechanisms. Meanwhile, the maintaining of the function of β-cells may also play a role in controlling the long-term postprandial hyperglycemia.

GLP-1 analogues are administered through subcutaneous injection, which doesn't require calculation of the amount of carbohydrates to estimate the optimal drug dosage, and does not require self-monitoring the blood glucose. As a result, these kinds of drugs are easier for patient compliance than self-administered insulin.

A variety of effects of natural GLP-1 have been confirmed, which bring new hope for the treatment of T2DM. The natural human GLP-1 peptide is, however, very unstable and can be degraded by dipeptidyl peptidase IV (DPP-IV). Moreover, its half-life is only about 2 minutes. When using natural GLP-1 to lower blood sugar, continuous intravenous infusion or continuous subcutaneous injection is needed, resulting in its poor clinical feasibility. Faced with this situation, researchers continue to explore methods to extend the action time of GLP-1. Therefore, there is a need for the development of long-acting GLP-1 analogues or derivatives thereof.

Exenatide is a synthetic Exendin-4, which is developed by the Eli Lilly Company and Amylin Company, with the trade name Byetta®. Exenatide has been approved for the treatment of T2DM by FDA and EMEA. It has 50% homology with mammalian GLP-1 in sequence and has a similar affinity site of the receptor with GLP-1. (See Drucker D J, Nauck M A. The incretin system: glucagon-like peptide-1 receptor agonists and dipeptidyl peptidase-4 inhibitors in type 2 diabetes. Lancet. 2006, 368(9548):1696-1705). It is encoded by a lizard-specific gene. Compared with GLP-1, the second residue, alanine, in GLP-1 is replaced with glycine in Exenatide, which effectively inhibits the enzymolysis of DPP-IV enzyme, and its half-life in vivo is about 60-90 minutes. (See Kolterman O G, Kim D D, Shen L, et al. Pharmacokinetics, pharmacodynamics, and safety of exenatide in patients with type 2 diabetes mellitus. Am Health Syst Pharm. 2005, 62(2): 173-181). The in vivo concentration of Exenatide after a single subcutaneous injection is increased persistently and can arrive to the maximum plasma concentration after 2 h or so, which can be maintained for 4-6 hours. (See Nielsen L L, Baron A D. Pharmacology of exenatide (synthetic exendin-4) for the treatment of type 2 diabetes. Curr Opin Investig Drugs. 2003, 4(4):401-05). It should be noted that the metabolism of Exenatide does not occur in the liver, but is degraded mainly by protein protease after filtered by renal glomeruli.

Exenatide has special glucose-regulating activities, including glucose-dependent enhance of insulin secretion, glucose-dependent inhibition of wrong excessive glucagon secretion, slowing gastric emptying and decreasing food intake and the like. Studies in vitro and in vivo in the models of diabetes found that Exenatide also has the effects of storing the first stage (first-phase) insulin secretion, promoting the proliferation of β-cell and promoting the regeneration of insulin from its precursor cell.

In order to achieve better control of blood glucose, injections twice a day of Exenatide are needed. This is a major inconvenience to patients. Furthermore, Exenatide has unfortunate side effects including mild to moderate nausea (about 40% of patients will have this reaction), diarrhea and vomiting (less than 15% of patients have both reactions). In addition, about 50% of Exenatide-treated patients can generate antibodies, although these antibodies do not affect the efficacy or lead to other clinical effects. Recently it is found that six patients suffered hemorrhage or symptoms of necrotizing pancreatitis after taking Byetta®.

CJC-1131 is a GLP-1 analogue with peptidase resistance developed by ConjuChem Biotechnologies Inc., in which the alanine residue in the second position of GLP-1 is replaced with D-Ala to enhance resistance of DPP-IV enzymolysis. The structure contains an active reactive linker that can bind to serum albuminutes through a covalent, non-reversible manner. (See Kim J G, Baggio L L, Bridon D P, et al. Development and characterization of a glucagon-like peptide-1 albuminutes conjugate: the ability to activate the glucagon-like peptide 1 receptor in vivo. Diabetes 2003, 52(3):751-759). The GLP-1-serum albuminutes complex retains the activity of GLP-1, while increasing its stability to DPP-IV enzymolysis, thereby extending in vivo action. Its half-life in plasma is about 20 days.

A study has found that the Ki was approximate 12 nM (the Ki of GLP-1 is 5.2 nM) when CJC-1131-serum albuminutes complex is bound to Chinese hamster ovary cell transfected with recombinant human pancreatic GLP-1 receptor. Meanwhile the $EC_{50}$ of the complex activating cAMP is 11-13 nM, wherein the $EC_{50}$ is similar to GLP-1's $EC_{50}$. Existing literature reports show that this complex can reduce postprandial blood glucose level of the mice whose blood sugar is normal or high, and tests show that this activity of CJC-1131 acts on a certain functional receptor of GLP-1. Meanwhile in mice, CJC-1131 also has an effect on slowing gastric emptying and inhibiting food intake and the like.

Part of a phase II clinical trial of CJC-1131 has been completed. In September 2005, ConjuChem concluded that CJC-1131 may not be suitable for chronic dosing regimens after analysis of test results and suspended further clinical study Albugon (albumin-GLP-1) is a long-acting drug for the treatment of T2DM developed by GlaxoSmithKline authorized by Human Genome Sciences Inc., which is a fusion protein of GLP-1 (with mutations increasing the resistance to DDP-IV) and albumin. Its half-life in monkeys is 3 days. The basic idea of the development thereof is to couple the recombinant GLP-1 and serum albuminutes to form a complex, thereby its in vivo half-life is significantly increased. The administration of Albugon effectively reduces blood glucose level of mice, increases insulin secretion, slows gastric emptying and reduces food intake etc. (See Baggio L L, Huang Q, Brown T J, et al. A Recombinant Human Glucagon-Like Peptide (GLP)-1-Albuminutes Protein (Albugon) Mimics Peptidergic Activation of GLP-1Receptor-Dependent Pathways Coupled With Satiety, Gastrointestinal Motility, and Glucose Homeostasis. Diabetes 2004, 53(9):2492-2500). Currently Albugon is in phase III clinical trials.

WO9808871 discloses a GLP-1 derivative which is obtained through the modification on GLP-1(7-37) with fatty acid. The half life in vivo of GLP-1 is significantly enhanced. WO9943705 discloses a derivative of GLP-1, which is chemically modified at the N-terminus, but some literature reports that modification of the amino acids on the N-terminal will significantly decrease the activity of the entire GLP-1 derivative. (See J. Med. Chem. 2000, 43, 1664 1669). In addition, CN200680006362, CN200680006474, WO2007113205, CN200480004658, CN200810152147 and WO2006097538 etc also disclose a series of GLP-1 analogues or derivatives thereof produced by chemical modification or amino acid substitution, in which the most representative one is liraglutide developed by Novo Nordisk, the phase III clinical trial of which has been finished. Liraglutide is a derivative of GLP-1, whose structure contains a GLP-1 analogue of which the sequence is 97% homologous with human GLP-1, and this GLP-1 analogue is linked with palmitic acid covalently to form Liraglutide, wherein the palmitic acid of the structure of Liraglutide is linked to serum albuminutes non-covalently, and this structural characteristic affects a slower release from the injection site without changing the activity of GLP-1 thereby extending its in vivo half life Meanwhile, the palmitic acid in the structure will form a certain steric hindrance to prevent the degradation by DPP-IV and to reduce renal clearance. Because of the characteristics described above, the half-life of Liraglutide in the human body administered by subcutaneous injection is about 10-14 hours. In theory, it can be administered once on day and the daily dose is 0.6-1.8 mg. On Apr. 23, 2009, Novo Nordisk announced that Committee for Medicinal products for Human Use (CHMP) under the EMEA gave a positive evaluation on Liraglutide and recommended approval of its listing. Novo Nordisk hopes that European Commission would approve its application of listing within two months.

BRIEF SUMMARY OF THE INVENTION

The present invention describes GLP-1 analogues which have longer half-life in vivo. The GLP-1 analogues described have the same function as that of human GLP-1 and a longer half-life in vivo.

The present invention also includes pharmaceutical compositions comprising GLP-1 analogues and pharmaceutically acceptable salts thereof, for use in the treatment of non-insulin-dependent diabetes mellitus, insulin-dependent diabetes and obesity.

The aims of the present invention are achieved by the following technical solutions. The present invention provides GLP-1 analogues having amino acid sequence of formula (I) or a pharmaceutically acceptable salt thereof:

Formula (I) - SEQ ID NO: 238
X1-X2-Glu-Gly-Thr-Phe-Thr-Ser-Asp-X10-Ser-X12-X13-

X14-Glu-X16-X17-Ala-X19-X20-X21-Phe-Ile-X24-Trp-

Leu-X27-X28-X29-X30-X31-X32-X33-X34-X35-X36-X37-

X38-X39-Lys wherein the GLP-1 analogues contain a lipophilic substituent of formula $R_1(CH_2)_n-CO-$, in which $R_1$ is selected from $CH_3-$ and HOOC—, n is an integer selected from 8-25, X1, X2, X10, X12, X13, X14, X16, X17, X19, X20, X21, X24, X27, X28, X29, X30, X31, X32, X33, X34, X35, X36, X37, X38 and X39 are independently selected from any natural or non-natural amino acid or the peptide segments consisting of any natural or non natural amino acid.

The GLP-1 analogues refer to a new GLP-1 peptide obtained by the partial amino acid substitution or the extension at the C terminal of human GLP-1 (7-37) peptide serving as a precursor, comprising GLP-1 (7-36) amide and GLP-1 (7-37), which has same function as that of human GLP-1.

The GLP-1 analogues may be modified so that amino acid residues have lipophilic substituents, wherein a typical modification is to form an amide or ester, preferably, to form an amide.

In a preferred embodiment of the invention, the lipophilic substituent of formula $R_1(CH_2)_n-CO-$ and the amino group of the amino acid residues of the GLP-1 analogue are linked by an amide bond, in which $R_1$ is selected from $CH_3-$ and HOOC—, and n is an integer selected from 8-25.

In another preferred embodiment of the invention, the lipophilic substituent of formula $R_1(CH_2)_n-CO-$ and the ε amino group of the Lys at the C-terminal of the GLP-1 analogue are linked by an amide bond, in which $R_1$ is selected from $CH_3-$ and HOOC—, and n is an integer selected from 8-25.

In yet another preferred embodiment of the invention, the lipophilic substituent of formula $R_1(CH_2)_n-CO-$ and the α amino group of the Lys at the C-terminal of the GLP-1 analogue are linked by an amide bond, in which $R_1$ is selected from $CH_3-$ and HOOC—, and n is an integer selected from 8-25, and 14 is the most preferred.

In another preferred embodiment of the invention, X1 in the amino acid sequence of the GLP-1 analogue is selected from L-His and D-His; X2 is selected from Ala, D-Ala, Gly, Val, Leu, Ile, Lys and Aib; X10 is selected from Val and Leu; X12 is selected from Ser, Lys and Arg; X13 is selected from Tyr and Gln; X14 is selected from Leu and Met; X16 is selected from Gly, Glu and Aib; X17 is selected from Gln, Glu, Lys and Arg; X19 is selected from Ala and Val; X20 is selected from Lys, Glu and Arg; X21 is selected from Glu and Leu; X24 is selected from Val and Lys; X27 is selected from Val and Lys; X28 is selected from Lys, Glu, Asn and Arg; X29 is selected from Gly and Aib; X30 is selected from Arg, Gly and Lys; X31 is selected from Gly, Ala, Glu, Pro and Lys; X32 is selected from Lys and Ser; X33 is selected from Lys and Ser; X34 is selected from Gly, Ala and Sar; X35 is selected from Gly, Ala and Sar; X36 is selected from Pro and Gly; X37 is selected from Pro and Gly; X38 is selected from Pro and Gly; X39 is selected from Ser and Tyr.

In one more preferred embodiment of the present invention, the amino acid sequence of the GLP-1 analogue is selected from the group consisting of SEQ ID NO: 1 to SEQ ID NO: 238.

In another preferred embodiment of the present invention, the lipophilic substituent of formula $R_1(CH_2)_n-CO-$ and the amino group of the amino acid residues of the GLP-1 analog, of which the sequence is selected from the group consisting of SEQ ID NO: 1 to SEQ ID NO: 238, are linked by an amide bond, in which $R_1$ is selected from $CH_3-$ and HOOC—, and n is an integer selected from 8-25.

In one more preferred embodiment of the present invention, the lipophilic substituent of formula $R_1(CH_2)_n-CO-$ and the α amino group of the C-terminal Lys of the GLP-1 analog, selected from the group consisting of SEQ ID NO: 1 to SEQ ID NO: 238, are linked by an amide bond, in which $R_1$ is selected from $CH_3-$ and HOOC—, and n is an integer selected from 8-25.

In one more preferred embodiment of the present invention, the lipophilic substituent of formula $R_1(CH_2)_n-CO-$ and the α amino group of the C-terminal Lys of the GLP-1 analog, selected from the group consisting of SEQ ID NO: 1 to SEQ ID NO: 238, are linked by an amide bond, in which $R_1$ is selected from $CH_3$ and HOOC—, and n is an integer selected from 8-25, preferably n is selected from 8, 10, 12, 14, 16, 18, 20 and 22, most preferably, n is 14.

In one more preferred embodiment of this invention, the lipophilic substituent of formula $R_1(CH_2)_n-CO-$ and the α amino group of the C-terminal Lys of the GLP-1 analog, selected from the group consisting of SEQ ID NO: 1 to SEQ ID NO: 20 and/or SEQ ID NO: 121 to SEQ ID NO: 136 and/or SEQ ID NO: 237, are linked by an amide bond, in which $R_1$ is selected from $CH_3-$ and HOOC—, and n is an integer selected from 8-25, preferably n is selected from 8, 10, 12, 14, 16, 18, 20 and 22, most preferably, n is 14.

In another more preferred embodiment of this invention, the lipophilic substituent of formula $R_1(CH_2)_n$—CO— and the α amido of the C-terminal Lys of the GLP-1 analog, selected from the group consisting of SEQ ID NO: 1 to SEQ ID NO: 8 and/or SEQ ID NO: 121 to SEQ ID NO: 124, are linked by an amide bond, in which $R_1$ is $CH_3$, and n is 14.

The GLP-1 analogues provided in this invention belong to amphoteric compounds and one skilled in the art can convert them into salts by using acid or alkaline compounds with known technologies, wherein acids usually used for the formation of acid addition salts are: hydrochloric acid, hydrobromic acid, hydriodic acid, sulfuric acid, phosphoric acid, p-toluenesulfonic acid, methanesulfonic acid, oxalic acid, p-bromophenyl sulfonic acid, carbonic acid, succinic acid, citric acid, benzoic acid, acetic acid; the salts comprise sulfate, pyrosulfate, trifluoroacetate, sulfite, bisulfate, phosphate, biphosphate, dihydric phosphate, metaphosphate, pyrophosphate, hydrochloride, bromide, iodide, acetate, propionate, octanoates, acrylate, formate, isobutyric acid, hexanoate, enanthates, propiolate, oxalate, malonate, succinate, suberate, fumarate, maleate, 1,4-butynedioate, 1,6-hexynedioate, benzoate, chloro-benzoate, methyl-benzoate, dinitro-benzoate, hydroxyl-benzoate, methoxy-benzoate, phenylacetate, phenpropionate, phenylbutyrate, citrate, lactate, γ-hydroxybutyrate, glycolate, tartrate, methanesulfonate, propanesulfonate, 1-naphthol-sulfonate, 2-naphthol-sulfonate, mandelate and the like, preferably trifluoroacetate. Alkaline substances can also be turned into salts with GLP-1 analogues, wherein the alkaline substances comprise ammonium, hydroxides of alkali metals or alkaline earth metal, and carbonate, bicarbonate, typically sodium hydroxide, potassium hydroxide, ammonium hydroxide, sodium carbonate, potassium carbonate and the like.

The pharmaceutical compositions containing GLP-1 derivatives according to the invention can be used to treat patients who need this treatment by the way of parenteral administration. Parenteral administration can be chosed from subcutaneous, intramuscular or intravenous injections. The GLP-1 derivatives of the invention can also be administered by transdermal routes, such as administration via transdermal patch (iontophoresis patch and others) and administration through the mucosa.

The pharmaceutical compositions containing the GLP-1 derivatives of the invention can be prepared through common techniques in the art of pharmaceutical industry. These techniques comprise proper dissolving and mixing the components to obtain the desired final compositions. For instance, the GLP-1 derivatives are dissolved in a certain amount of water, wherein the volume of water is slightly less than the final volume of the obtained composition. Isotonic agents, preservatives, surfactants and buffers are added according to need, wherein said isotonic agents are sodium chloride, mannitol, glycerol, propylene glycol, sugar or alditol. Said preservatives are phenol, orthocresol, para-cresol, meta-cresol, methylparahydroxybenzoate ester, benzyl alcohol. Said appropriate buffering agents are sodium acetate, sodium carbonate, glycine, histidine, lysine, sodium dihydrogen phosphate, disodium hydrogen phosphate, sodium phosphate. Said surfactants are Poloxamer, Poloxamer-188, Poloxamer-407, Tween 80 and Tween-20. If necessary, the aqueous solutions of acids such as hydrochloric acid or alkali such as sodium hydroxide solution are added to adjust pH values of the solutions, and finally the solution volume is adjusted by adding water to obtain the required concentration. Besides said components, the pharmaceutical compositions of the invention also comprise enough basic amino acids or other alkaline reagents having the function to decrease the aggregates formed by the composition during storage, such as lysine, histidine, arginine, imidazole during storage.

The GLP-1 analogues of the invention can be synthesized manually, wherein the resin is HMPA-AM resin, the α-amino group of the amino acid derivatives is protected by the Fmoc (fluorene formyl carbonyl), the side-chain thiol of cysteine, the side-chain amido of glutamine, the side-chain imidazole of histidine are protected by Trt (triphenylmethyl), the side-chain guanidyl of arginine is protected by Pbf (2,2,4,6,7-pentamethyl-dihydrobenzofuran-5-sulfonyl). The side-chain indolyl of tryptophan and the side-chain amino group of lysine are protected by Boc (tert-Butoxycarbonyl) (the side-chain amino group of the Lys are protected by Mtt when the peptide backbone is formed through ε amino group of Lys), the side-chain hydroxyl of threonine, the side-chain phenylol of tyrosine, the side-chain hydroxyl of serine are protected by tBu (tert-butyl). The carboxyl of C-terminal amino acids of the peptide chain of the GLP-1 analogues which will be synthesized is connected with an insoluble high molecular resin (HMP-AM resin) through covalent bonds, and then, the amino acids bound to a solid phase carrier act as amino components, the amino protection group is removed by 20% Hexahydropyridine/DMF solution, and then reactes with excess amino acid derivatives to link a long peptide chain. The operation (Condensation→washing→deprotection→washing→next round of condensation) is repeated to achieve the peptide chain length desired. Finally, the peptide chain is cleaved down from the resins by using mixture of TFA:water:1,2-dithioglycol:triisopropylsilane (92.5:2.5:2.5:2.5), to obtain the crude GLP-1 analogues through precipitation in an ether. The crude products are purified through using C18 reversed-phase column, and thereby obtaining the desired GLP-1 analogues. The ninhydrin testing method was used to moniter the condensation and the deprotection steps—that is, when there are free aminos on the resin, the ninhydrin reagent will show blue and no color (or slightly yellow) will be shown when there are no free aminos on the resin (Ninhydrin reagent itself is yellow). Therefore, after the condensation reaction is completed, if it shows yellow through ninhydrin test (color of Ninhydrin reagent per se), then it suggests that the coupling step is completed and the deprotection operation before next amino acid coupling can be carried out. If the testing shows blue, it suggests that there are still some free aminos on the peptide chains, and it is needed to further repeat the coupling step or to change the existing condensing agent until the testing has no color or slightly yellow.

DETAILED DESCRIPTION OF THE INVENTION

To describe the present invention in more detail, the following examples are provided. However, the present invention should not be construed as limited to the embodiments set forth herein.

EXAMPLE 1

The Method for Solid-Phase Synthesis of HS-20001

1. Preparation of Fmoc-Lys (Mtt)-HMP-AM Resin
(1) Drying and Swelling of HMP-AM Resin
50 g (30 mmol) HMP-AM resin (0.6 mmol/g) was dried for 24 hours in vacuum and placed into a 2 L bubbling bottle. Resins were swelled with 500 mL N,N-dimethylformamide (DMF) for 30 minutes, then the DMF was drawn-off and the resins were washed with DMF for 1 minute. The washing step was repeated twice.

2. Preparation of Fmoc-Lys(Mtt)-HMP-AM Resin (1) Coupling of Fmoc-Lys (Mtt)-OH with HMP-AM Resin The resins were washed with 500 mL DCM and then the washing step was repeated twice. 56.2 g (90 mmol) Fmoc-Lys(Mtt)-OH and 11.4 g (90 mmol) DIC were dissolved in 1 L DCM and added into the swelled HMP-AM resin. 366 mg (3 mmol) DMAP were added to react for 24 hours.

(2) Washing of the Resin

After the reaction, the resin was washed alternately with DMF and IPA twice and washed with DMF 3 times.

(3) Capping of Hydroxyl 15.3 g (150 mmol) acetic anhydride and 19.4 g (150 mmol) DIEA were dissolved in 1 L DMF and added into the resin to react for 10 min.

(4) Washing of the Resin

The resin was washed twice with 1 L 50% MeOH/DMF, 50% DCM/DMF, and then washed three times with DCM and with dehydrated ethanol three times successively. The resin was then dried under vacuum to obtain the Fmoc-Lys(Mtt)-HMP-AM resin.

(5) Loading Assays of Fmoc-Lys(Mtt)-HMP-AM Resin

5~10 mg resin were put into 1 mL 20% Hexahydropyridine/DMF solution and stirred for 20 minutes. 50 mL supernatant was removed with a pipet and diluted in 2.5 mL DMF.

Blank samples: 50 mL 20% Hexahydropyridine/DMF was taken with a pipet and is diluted in 2.5 mL DMF.

Degree of substitution is calculated as follows:

$$Sub=(A\times51)/(7.8\times m)$$

wherein A is the absorption value of UV at 301 nm; m is the weight of the resin in mg.

2. Swelling of the Solid-Phase Synthesized Resin 50 g (20 mmol) Fmoc-Lys(Mtt)-HMPA-AM resin (0.4 mmol/g) was dried in vacuum for 24 hours and placed into a 2 L bubbling bottle. 500 mL N,N-dimethylformamide (DMF) were added to swell the resin for 30 minutes. The DMF solution was then drawn-off.

3. Removal of 4-Methyl Triphenylmethyl (Mtt) Protecting Group of Fmoc-Lys (Mtt)-HMPA-AM Resin The resin was washed with 200 mL DCM twice followed by addition of 1200 mL 1% TFA/DCM (TFA is about 8-fold excess) to remove Mtt protecting group for 1 hour. The resin was alternately washed with 200 mL 5% N,N-diisopropyl ethylamine (DIEA)/DMF and DMF three times followed by DMF washing three times.

4. Palmitic Acid Condensation 50 mmol palmitic acid and 50 mmol 3-(diethoxyphosphoryloxy)-1,2,3-phentriazine-4-ketone (DEPBT) were dissolved in 400 mL DMF. Then 100 mmol DIEA were added and stirred for 3 minutes at room temperature. The solution was added to the resin, reacted in 37° C. water baths for 2 hours under $N_2$. After the reaction, the reaction solution was drawn-off and the resin was washed with DMF, isopropyl alcohol (IPA), and DMF in turn.

5. \Removal of 9-Fmoc (Fluorenylmethyloxycarbonyl) Protecting Group of Fmoc-Lys (N-ϵ-Palmitic Acid)-HMPA-AM Resin 200 mL 20% piperidine/DMF solution were placed into a bubbling bottle filled with Fmoc-Lys (N-ϵ-palmitic acid)-HMPA-AM resin and reacted for 5 minutes and then is drawn out. Then 200 mL 20% piperidine/DMF solution were added to react for 20 minutes at room temperature. After the reaction, the resin was washed with 200 mL DMF four times.

6. Solid Phase Synthesis of Peptide Chain Part of HS-20001

(1) Condensation of Fmoc-Ser (tBu)-OH 50 mmol Fmoc-Ser(tBu)-OH were dissolved in 125 mL 0.4 M 1-hydroxybenzo triazole (HOBt)/DMF. Then 125 mL 0.4 M N,N'-diisopropyl carbodiimide (DIC)/DCM were added to activate and react for 10 minutes at room temperature. The solution was added into the resin, reacted under of nitrogen at room temperature. Ninhydrin was used to detect and control the degree of the reaction. After reaction, the reaction solution was removed, and the resin was washed with DMF, IPA and DMF in turn.

(2) Extension of the Peptide Chain

HS-20001 resin peptide was synthesized according to the sequence of the peptide chain of HS-20001 from the amino terminal (N-terminal) to the carboxy-terminal (C-terminal) (His-(D)-Ala-Glu-Gly-Thr-Phe-Thr-Ser-Asp-Leu-Ser-Lys-Gln-Nle-Glu-Glu-Glu-Ala-Val-Arg-Leu-Phe-Ile-Glu-Trp-Leu-Lys-Gln-Gly-Gly-Pro-Ser-Ser-Gly-Ala-Pro-Pro-Pro-Ser), wherein the amounts of amino acids and condensation reagents were the same as the amounts for Fmoc-Ser (tBu)-OH. Protected amino acids were Fmoc-Pro-OH, Fmoc-Ala-OH, Fmoc-Gly-OH, Fmoc-Ser(tBu)-OH, Fmoc-Gln(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Arg(Pbf)-OH, Fmoc-Val-OH, Fmoc-Nle-OH, Fmoc-Asp(OtBu)-OH, Fmoc-Thr(tBu)-OH, Fmoc-D-Ala-OH and Fmoc-His(Trt)-OH respectively, and condensation and deprotection reactions were repeated.

(3) Post-Processing of HS-20001 Resin Peptide

HS-20001 resin peptide obtained in step (2) was washed with DMF, IPA and DMF in turn, then washed with absolute ether twice, and dried under vacuum to obtain the HS-20001 resin peptide.

(4) Preparation of HS-20001 Crude Peptide

The dried HS-20001 peptide resin is reacted with fresh lysate), of trifluoroacetic acid (TFA):triisopropylsilane (TIS): water=95:2.5:2.5 (by volume and total 10 mL of lysate per gram of the dry resin) for 4 h at room temperature. The reaction solution was filtrated, and the resin was washed with TFA twice. The filtrate was collected, combined, and concentrated to ⅓ of the original volume through rotary evaporation. HS-20001 was precipitated and washed with cold absolute ether, after centrifugation and drying in vacuum, white crude HS-20001 was obtained.

(5) Preparation of HS-20001 with Reversed-Phase Liquid Chromatography 10 g crude HS-20001 was dissolved in a certain amount of water, filtrated with 0.45 μm membrane filter, then purified with reversed-phase high performance liquid chromatography (RP-HPLC), wherein the mobile phase is A 0.1% TFA/$H_2O$, B 0.1% TFA/acetonitrile, the column is Denali C-18 column (particle diameter 8.3 μm, 5×30 cm), column temperature is 45° C., detection wavelength is 220 nm, flow rate is 120 mL/min. The product peaks were collected and concentrated under vacuum to remove most of the acetonitrile. 2.25 g of the product (HS-20001) was obtained by lyophilization, of which the purity as 98.5%, and the yield was 22.5%.

EXAMPLE 2

The Solid-Phase Synthesis Method for HS-20002

1. Preparation of Fmoc-Lys (Mtt)-HMP-AM Resin

See Example 1.

2. Swelling of the Solid-Phase Synthesized Resin 50 g (20 mmol) Fmoc-Lys(Mtt)-HMPA-AM resin (0.4 mmol/g) was dried for 24 hours in vacuum and placed into a 2 L bubbling bottle. The resin was swelled with 500 mL DMF for 30 minutes, and then DMF solution was drawn-off.

3. Removal of Mtt Protecting Group of Fmoc-Lys(Mtt)-HMPA-AM Resin

The resin was washed with 200 mL DCM twice. Mtt protecting group was removed by adding 1200 mL 1% TFA/

DCM (TFA is about 8-fold excess) for 1 hour, and then washed with 200 mL 5% DIEA/DMF and DMF alternately for three times followed by DCM washing three times.

4. Palmitic Acid Condensation 50 mmol palmitic acid and 50 mmol DEPBT were dissolved in 400 mL DMF, and then 100 mmol DIEA was added by stirring to react for 3 minutes at room temperature. The resulting solution was added to the resin and reacted in 37° C. water bath under $N_2$ for 2 hours. After the reaction, the reaction solution as removed, and the resin was washed with DMF, isopropyl alcohol (IPA), and DMF in turn.

5. Removal of Fmoc Protecting Group of Fmoc-Lys (N-ε-Palmitic Acid)-HMPA-AM Resin 200 mL 20% Piperidine/DMF solution was placed into a bubbling bottle filled with Fmoc-Lys(N-ε-palmitic acid)-HMPA-AM resin, and drawn-off after reacting for 5 minutes. 200 mL 20% Piperidine/DMF solution was added for reacting for 20 minutes at room temperature. After the completion, the resin was washed four times with 200 mL DMF.

6. Solid-Phase Synthesis Method for the Peptide Chain Part of HS-20002

(1) Condensation of Fmoc-Ser (tBu)-OH 50 mmol Fmoc-Ser(tBu)-OH were dissolved in 125 mL 0.4M HOBt/DMF, then 125 mL 0.4 M DIC/DCM were added to activate and react for 10 minutes at room temperature. The resulting solution was contacted with the resin and reacted under $N_2$ at room temperature. Ninhydrin was used to detect and control the degree of the reaction. After the reaction, the reaction solution as removed, and the resin was washed with DMF, IPA and DMF in turn.

(2) Extension of the Peptide Chain

HS-20002 resin peptide was synthesized according to the sequence of peptide chain of HS-20002 from the N-amino (N-terminal) to the carboxy-terminal (C-terminal) (His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser), wherein the amounts of amino acids and condensation reagents were the same as that of Fmoc-Ser (tBu)-OH, protected amino acids were Fmoc-Pro-OH, Fmoc-Ala-OH, Fmoc-Gly-OH, Fmoc-Ser(tBu)-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Arg(Pbf)-OH, Fmoc-Val-OH, Fmoc-Met-OH, Fmoc-Gln(Trt)-OH, Fmoc-Asp(OtBu)-OH, Fmoc-Thr(tBu)-OH and Fmoc-His(Trt)-OH respectively, and condensation and deprotection reactions were repeated.

(3) Post-Processing of HS-20002 Resin Peptide

The HS-20002 resin peptide obtained in step (2) was washed with DMF, IPA and DMF in turn, then washed twice with absolute ether, then dried under vacuum. HS-20002 resin peptide was obtained therefrom.

(4) Preparation of HS-20002 Crude Peptide

The dried HS-20002 peptide resin was reacted with fresh lysate of trifluoroacetic acid (TFA):triisopropylsilane (TIS):water:1,2-ethanedithiol (EDT)=94:1:2.5:2.5 (by volume and total 10 mL of lysate per gram of the dry resin) for 4 hours at room temperature. The reaction solution was filtrated after the reaction. The resin was washed with TFA twice, and then filtrate was collected, combined, and concentrated to ⅓ of the original volume through rotary evaporation. HS-20002 was precipitated with cold absolute ether, after centrifugation and drying under vacuum. The resulting product was white crude HS-20002.

(5) Preparation of HS-20002 with Reversed-Phase Liquid Chromatography 10 g crude HS-20002 were dissolved in a certain amount of water, filtrated with 0.45 μm membrane filter, then purified with reversed-phase high performance liquid chromatography (RP-HPLC), with a mobile phase A was 0.1% TFA/$H_2O$, B 0.1% TFA/acetonitrile, the column was a Denali C-18 column (particle diameter 8.3 μm, 5×30 cm), column temperature was 45° C., detection wavelength was 220 nm, flow rate was 120 mL/min. The product peaks were collected, concentrated under vacuum to remove most of acetonitrile. 2.1 g of HS-20002 was obtained by lyophilization, of which the purity was 98%, and the yield was 20.5%.

EXAMPLE 3

The Solid-Phase Synthesis Method for HS-20003

1. Preparation of Fmoc-Lys (Mtt)-HMP-AM Resin
See Example 1.

2. Swelling of the Solid-Phase Synthesized Resin 50 g (20 mmol) Fmoc-Lys(Mtt)-HMPA-AM resin (0.4 mmol/g) dried for 24 hours in vacuum were placed into a 2 L bubbling bottle. The resin was swelled with 500 mL DMF for 30 minutes, and then DMF solution was drawn-off.

3. Removal of Fmoc Protecting Group of Fmoc-Lys(Mtt)-HMPA-AM Resin 200 mL 20% piperidine/DMF solution were added into a bubbling bottle filled with Fmoc-Lys (Mtt)-HMPA-AM resin. Then the solution was drawn off after 5 minutes, and 200 mL 20% piperidine/DMF solution were added. The reaction continued for another 20 minutes at room temperature. After the reaction, the resin was washed four times with 200 mL DMF.

4. Palmitic Acid Condensation 50 mmol Palmitic acid and 50 mmol DEPBT were dissolved in 400 mL DMF. Then 100 mmol DIEA was added by stirring to react for 3 minutes at room temperature. The resulting solution was added to the resin, reacted in 37° C. water baths under $N_2$ for 2 hours. After the reaction, the reaction solution was removed, and the resin was washed with DMF, isopropyl alcohol (IPA), and DMF in turn.

5. Removal of Mtt Protecting Group of N-α-Palmitic Acid-Lys(Mtt)-HMPA-AM Resin

The resin was washed with 200 mL DCM twice. The Mtt protecting group was removed by adding 1200 mL 1% TFA/DCM (TFA is about 8-fold excess) for 1 hour. The resin was washed with 200 mL 5% DIEA/DMF and DMF alternately three times, then washed with DCM three times.

6. Solid-Phase Synthesis Method for the Peptide Chain Part of HS-20003

(1) Condensation of Fmoc-Ser (tBu)-OH 50 mmol Fmoc-Ser(tBu)-OH and 50 mmol DEPBT were dissolved in a certain amount of DCM. Then 100 mmol DIEA was added for activation for 3 minutes at room temperature. The solution was added to the resin, reacted under $N_2$ at room temperature, and ninhydrin was used to detect and control the degree of the reaction. After the reaction, the reaction solution was removed, and the resin was washed with DMF, IPA and DMF in turn.

(2) Extension of the Peptide Chain

HS-20003 resin peptide is synthesized according to the sequence of peptide chain of HS-20003 from the N-amino (N-terminal) to the carboxy-terminal (C-terminal) (His-(D)-Ala-Glu-Gly-Thr-Phe-Thr-Ser-Asp-Val-Ser-Ser-Tyr-Leu-Glu-Glu-Glu-Ala-Ala-Lys-Glu-Phe-Ile-Ala-Trp-Leu-Val-Arg-Gly-Gly-Pro-Ser-Ser-Gly-Ala-Pro-Pro-Pro-Ser),
wherein the amounts of amino acids and condensation reagents were the same as that of Fmoc-Ser (tBu)-OH, protected amino acids were Fmoc-Pro-OH, Fmoc-Ala-OH, Fmoc-Gly-OH, Fmoc-Ser(tBu)-OH, Fmoc-Arg(Pbf)-OH, Fmoc-Val-OH, Fmoc-Leu-OH, Fmoc-Trp(Boc)-OH, Fmoc-Ile-OH, Fmoc-Phe-OH, Fmoc-Glu(OtBu)-OH, Fmoc-Lys (Boc)-OH, Fmoc-Tyr(tBu)-OH, Fmoc-Asp(OtBu)-OH, Fmoc-Thr(tBu)-OH respectively, and condensation and deprotection reactions were repeated.

(3) Post-Processing of HS-20003 Resin Peptide

The HS-20003 resin peptide obtained in step (2) was washed with DMF, IPA and DMF in turn, then washed twice with absolute ether, and dried under vacuum to obtain HS-20003 resin peptide.

(4) Preparation of HS-20003 Crude Peptide

The dried HS-20003 peptide resin was reacted with fresh lysate of trifluoroacetic acid (TFA):triisopropylsilane (TIS): water=95:2.5:2.5 (by volume and total 10 mL of lysate per gram of the dry resin) for 4 hours at room temperature. The reaction solution was filtrated after the reaction. The resin was twice washed with TFA. The filtrate was collected, combined, and concentrated to ⅓ of the original volume through rotary evaporation. HS-20003 was precipitated with cold ether under stirring. After centrifugation and drying in vacuum, white crude HS-20003 was obtained.

(5) Preparation of HS-20003 with Reversed-Phase Liquid Chromatography 10 g crude HS-20003 was dissolved in a certain amount of 20% acetic acid/water and stirred for at least 4 hours, then filtrated with 0.45 μm membrane filter, then purified with reversed-phase high performance liquid chromatography (RP-HPLC), wherein the mobile phase was A 0.1% TFA/H$_2$O, B 0.1% TFA/acetonitrile, the column was Denali C-18 column (particle diameter 8.3 mm, 5×30 cm), column temperature was 45° C., detection wavelength was 220 nm, flow rate was 120 mL/min. The product peaks were collected, concentrated with vacuum to remove most of acetonitrile. 2.5 g of HS-20003 was obtained by lyophilization, of which the purity was 98.5%, and the yield was 25%.

EXAMPLE 4

The Solid-Phase Synthesis Method for HS-20004

1. Preparation of Fmoc-Lys (Mtt)-HMP-AM Resin
See Example 1.
2. Swelling of the Solid-Phase Synthesized Resin 50 g (20 mmol) Fmoc-Lys(Mtt)-HMPA-AM resin (0.4 mmol/g) dried for 24 hours under vacuum were placed into a 2 L bubbling bottle. 500 mL DMF was added to swell the resin for 30 minutes, followed by drawing off DMF solution.

3. Removal of Fmoc Protecting Group of Fmoc-Lys(Mtt)-HMPA-AM Resin 200 mL 20% piperidine/DMF solution were added into a bubbling bottle filled with Fmoc-Lys (Mtt)-HMPA-AM resin, and then drawn off after 5 minutes, and then 200 mL 20% piperidine/DMF solution was added for reacting for 20 minutes at room temperature. After the reaction, the resin was washed four times with 200 mL DMF.

4. Palmitic Acid Condensation 50 mmol palmitic acid and 50 mmol DEPBT were dissolved in 400 mL DMF, and then 100 mmol DIEA was added by stirring for 3 minutes at room temperature. The resulting solution was added to the resin, reacted in 37° C. water bath under N$_2$ for 2 hours. After the reaction, the reaction solution was removed, and the resin was washed with DMF, isopropyl alcohol (IPA) and DMF in turn.

5. Removal of Mtt Protecting Group of Palmitic Acid-Lys (Mtt)-HMPA-AM Resin

The resin was washed with 200 mL DCM twice. Mtt protecting group was removed by adding 1200 mL 1% TFA/DCM (TFA is about 8-fold excess) for reacting for 1 hour, then washed with 5% DIEA/DMF and DMF alternately for three times, then washed three time with DCM.

6. The Solid-Phase Synthesis Method for the Peptide Chain Part of HS-20004

(1) Condensation of Fmoc-Ser (tBu)-OH 50 mmol Fmoc-Ser(tBu)-OH and 50 mmol DEPBT were dissolved in a certain amount of DCM. Then 100 mmol DIEA was added for activation for 3 minutes at room temperature. The resulting solution was added to the resin, reacted under N$_2$ at room temperature, and ninhydrin was used to detect and control the degrees of the reaction. After the reaction, the reaction solution was removed, and the resin was washed with DMF, IPA and DMF in turn.

(2) Extension of the Peptide Chain

HS-20004 resin peptide was synthesized according to the sequence of the peptide chain of HS-20004 from the N-amino (N-terminal) to the carboxy-terminal (C-terminal) (His-Aib-Glu-Gly-Thr-Phe-Thr-Ser-Asp-Val-Ser-Ser-Tyr-Leu-Glu-Glu-Glu-Ala-Ala-Lys-Glu-Phe-Ile-Ala-Trp-Leu-Val-Arg-Gly-Gly-Pro-Ser-Ser-Gly-Ala-Pro-Pro-Pro-Ser), wherein the amounts of amino acids and condensation reagents were same as that of Fmoc-Ser (tBu)-OH. Protected amino acids were Fmoc-Pro-OH, Fmoc-Ala-OH, Fmoc-Gly-OH, Fmoc-Ser(tBu)-OH, Fmoc-Arg(Pbf)-OH, Fmoc-Val-OH, Fmoc-Leu-OH, Fmoc-Trp(Boc)-OH, Fmoc-Ile-OH, Fmoc-Phe-OH, Fmoc-Glu(OtBu)-OH, Fmoc-Lys(Boc)-OH, Fmoc-Tyr (tBu)-OH, Fmoc-Asp(OtBu)-OH, Fmoc-Thr(tBu)-OH, Fmoc-Aib-OH and Fmoc-His(Trt)-OH respectively, and the condensation and deprotection reactions were repeated.

(3) Post-Processing for HS-20004 Resin Peptide

HS-20004 resin peptide obtained in step (2) was washed with DMF, IPA and DMF in turn, then washed twice with absolute ether, followed by drying under vacuum to obtain HS-20004 resin peptide.

(4) Preparation of Crude HS-20004 Peptide

The dried HS-20004 resin peptide was reacted with fresh lysate of trifluoroacetic acid (TFA):triisopropylsilane (TIS): water=95:2.5:2.5 (by volume and total 10 mL of lysate per gram of the dry resin) for 4 hours at room temperature. The reaction solution was filtrated, and the resin was washed twice with TFA. The filtrate was collected, combined, and concentrated to ⅓ of the original volume through rotary evaporation. HS-20004 was precipitated with cold ether under stirring. After centrifugation and drying in vacuum, white crude HS-20004 was obtained.

(5) Preparation of HS-20004 with Reversed-Phase Liquid Chromatography 10 g crude HS-20002 was dissolved in a certain amount of 20% acetic acid/water and stirred for at least 4 hours, then filtrated with 0.45 μm membrane filter, and purified with reversed-phase high performance liquid chromatography (RP-HPLC), wherein mobile phase was A 0.1% TFA/H$_2$O, B 0.1% TFA/acetonitrile, the column was Denali C-18 column (particle diameter 8.3 μm, 5×30 cm), column temperature was 45° C., detection wavelength was 220 nm, flow rate was 120 mL/min. The product peaks were collected, concentrated with under vacuum to remove most of acetonitrile. 2.25 g of HS-20004 was obtained by lyophilization, of which the purity was 98.5%, and the yield was 22.5%.

EXAMPLE 5

The Solid-Phase Synthesis Method for HS-20005

The preparation method of HS-20005 is as same as that described in example 4, wherein the difference is that the amino acid sequence is replaced with SEQ ID NO: 5, and 2.5 g HS-20005 product was obtained, the purity of which was 98.5%, and the yield was 25%.

EXAMPLE 6

The Solid-Phase Synthesis Method for HS-20006

The preparation method of HS-20006 was the same as that described in example 4, wherein the difference was that the amino acid sequence was replaced with SEQ ID NO: 6. 2.25 g of HS-20006 product was obtained, the purity of which is 98.5%, and the yield is 22.5%.

EXAMPLE 7

The Solid-Phase Synthesis Method for HS-20007

The preparation method of HS-20007 was the same as that described in example 4, wherein the difference is that the amino acid sequence was replaced with SEQ ID NO: 7. 2.1 g of HS-20007 product was obtained, the purity of which was 98%, and the yield was 20.5%.

EXAMPLE 8

The Solid-Phase Synthesis Method for HS-20008

The preparation method of HS-20008 was the same as that described in example 4, wherein the difference is that the amino acid sequence was replaced with SEQ ID NO: 8. 2.5 g of HS-20008 product was obtained, the purity of which was 98.5%, and the yield was 25%.

REFERENCE EXAMPLE

Solid-Phase Synthesis Method for Liraglutide

1. Preparation of Fmoc-Lys(Mtt)-HMP-AM Resin
(1) Drying and Swelling of HMP-AM Resin
50 g (30 mmol) HMP-AM resin (0.6 mmol/g) was dried for 24 hours in vacuum and placed into a 2 L bubbling bottle. 500 mL N,N-dimethylformamide (DMF) was added to swell therein for 30 minutes. The DMF solution was drawn-off, and DMF was added to wash the resin for 1 minute. This washing step was repeated twice.
(2) Preparation of Fmoc-Lys(Mtt)-HMP-AM Resin
① Coupling of Fmoc-Lys (Mtt)-OH and HMP-AM Resin
The resin was washed three times with 500 mL DCM/56.2 g (90 mmol) Fmoc-Lys(Mtt)-OH and 11.4 g (90 mmol) DIC were dissolved in 1 L DCM, and then added into the swelled HMP-AM resin. 366 mg (3 mmol) DMAP was added and reaction proceeded for 24 hours.
② Washing of the Resin
After the reaction, the resin was washed twice alternately with DMF and IPA and then washed three times with DMF.
③ Capping of Hydroxyl
15.3 g (150 mmol) acetic anhydride and 19.4 g (150 mmol) DIEA were dissolved in 1 L DMF and added to the resin for reacting for 10 minutes.
④ Washing of the Resin
The resin was washed twice with 1 L 50% MeOH/DMF, 50% DCM/DMF, three times with DCM, and was washed three times with absolute ethanol. It was then dried under vacuum to obtain the Fmoc-Lys(Mtt)-HMP-AM resin.

(3) Loading Assays of Fmoc-Lys(Mtt)-HMP-AM Resin
5~10 mg resin were put into 1 mL 20% Hexahydropyridine/DMF solution and stirred for 20 minutes. 50 μL supernatant is taken with a pipet and diluted in 2.5 mL DMF.
Blank samples: 50 μL 20% Hexahydropyridine/DMF was taken with a pipet and is diluted in 2.5 mL DMF.
Degree of substitution is calculated as follows:

$$Sub=(A\times51)/(7.8\times m)$$

wherein A is the absorption value of UV at 301 nm; m is the weight of the resin in mg.

2. Swelling the Resin of the Solid-Phase Synthesis
50 g (20 mmol) Fmoc-Gly-HMP-AM resin (0.4 mmol/g) dried for 24 hours in vacuum were placed into a 2 L bubbling bottle, and then 500 mL N,N-dimethylformamide (DMF) was added to swell the resin for 30 minutes. Thereafter, the DMF solution was drawn-off.

3. The Solid Phase Synthesis Method of the Peptide Chain Part of Liraglutide
① Condensation of Fmoc-Arg(Pbf)-OH
50 mmol Fmoc-Arg(Pbf)-OH were dissolved in 125 mL 0.4M 1-hydroxybenzotriazole (HOBt)/DMF, then 125 mL 0.4M N,N'-diisopropylcarbodiimide (DIC)/DCM were added to activate and react for 10 minutes at room temperature. The resulting solution was added to the resin, reacted under $N_2$ at room temperature, and ninhydrin was used to detect and control the degrees of the reaction. After the reaction, the reaction solution was drawn off, and the resin was washed with DMF, IPA and DMF in turn.
② Extension of the Peptide Chain
Precursor peptide of Liraglutide was synthesized according to the sequence of the peptide chain of Liraglutide from the N-amido (N-terminal) to the carboxy-terminal (C-terminal)
(His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Arg-Gly-Arg-Gly), wherein the amounts of amino acids and condensation reagents were the same as that of Fmoc-Arg(Pbf)-OH, protected amino acids were Fmoc-Arg(Pbf)-OH, Fmoc-Val-OH, Fmoc-Leu-OH, Fmoc-Trp(Boc)-OH, Fmoc-Ala-OH, Fmoc-Ile-OH, Fmoc-Phe-OH, Fmoc-Glu(OtBu)-OH, Fmoc-Lys(Mtt)-OH, Fmoc-Gln(Trt)-OH, Fmoc-Tyr(tBu)-OH, Fmoc-Ser(tBu)-OH, Fmoc-Asp(OtBu)-OH, Fmoc-Thr(tBu)-OH, Fmoc-His(Trt)-OH respectively, and the condensation and deprotection reactions were repeated.
③ Removal of Mtt Protecting Group of the Precursor Peptide of Liraglutide
The resin was twice washed with 200 mL DCM. The Mtt protecting group was removed twice by adding 1200 mL 1% TFA/DCM (TFA is about 8-fold excess) to react for 1 hour. The resin was washed alternately with 200 mL 5% N,N-diisopropylethylamine (DIEA)/DMF and DMF for three times, and washed 3 times with DMF.
④ Modification of Precursor Peptide of Liraglutide with Palmitic Acid
50 mmol Fmoc-Glu-OtBu were dissolved in 125 mL 0.4 M 1-hydroxybenzo triazole (HOBt)/DMF. Then 125 mL 0.4M N,N'-diisopropylcarbodiimide (DIC)/DCM was added to activate and react for 10 minutes at room temperature. The solution was added to the resin from step ③, and allowed to react under $N_2$ at room temperature. Ninhydrin was used to detect and control the degree of the reaction or reaction progress. After the reaction, the reaction solution was drawn-off, and the resin is washed with DMF, IPA and DMF in turn.

1 L 20% PIP/DMF was added to remove Fmoc protecting group for 5 minutes, then drawn off. 1 L of 20% PIP/DMF was added to remove Fmoc protecting group for 20 minutes, then are drawn off. The resulting resin was wased four times with DMF.

50 mmol palmitic acid and 50 mmol 3-(diethoxyphosphoryloxy)-1,2,3-phentriazine-4-ketone (DEPBT) was dissolved in 400 mL DMF. Then 100 mmol DIEA was added to react for 3 minutes under stirring at room temperature. The solution was added to the resin, reacted in 37° C. water bath under $N_2$ for 2 hours. After the reaction, the reaction solution was drawn-off, and the resin was washed with DMF, isopropyl alcohol (IPA), and DMF in turn.

4. Post-Processing of the Resin Peptide of Liraglutide

The resin peptide of Liraglutide obtained in step (2) was washed with DMF, IPA and DMF in turn, and then washed three times with DCM, washed twice with absolute ether, and dried in vacuum, to give the resin peptide of Liraglutide.

5. Preparation of Crude Peptide of Liraglutide

The dried peptide resin of Liraglutide was reacted with fresh lysate of trifluoroacetic acid (TFA):triisopropylsilane (TIS):water=95:2.5:2.5 (by volume and total 10 mL of lysate per gram of the dry resin) for 4 hours at room temperature. The reaction solution was filtrated after the reaction, and the resin was twice washed with TFA. The filtrate was collected, combined, and concentrated to ⅓ of the original volume through rotary evaporation. Liraglutide was precipitated with cold absolute ether, after centrifugation and drying under vacuum as white crude HS-20001 is obtained.

⑤ Preparation of Liraglutide with Reversed-Phase Liquid Chromatography 10 g of crude Liraglutide as dissolved in a certain amount of $NH_4HCO_3$ solution, filtrated with 0.45 μm membrane filter, then purified with reverse-phase high performance liquid chromotagraphy (RP-HPLC), wherein mobile phase was A 0.1% $TFA/H_2O$, B 0.1% TFA/acetonitrile, the column was Denali C-18 column (particle diameter 8.3 μm, 5×30 cm), column temperature was 45° C., detection wavelength was 220 nm, flow rate was 120 mL/min. The product peaks were collected, concentrated with vacuum to remove most of acetonitrile. 2.25 g of Liraglutide product was obtained by lyophilizatiom, the purity of which was 98%, and the yield was 12.5%.

Experimental Example 1

Testing the Agonist Activity of the Compounds on Glucagon-Like Peptide-1 Receptor (GLP1R)

GLP1R is a receptor coupled with Gs protein, of which the binding with the agonists will result in an increase of intracellular cAMP concentration. In the present experiment, GLP1R and the luciferase reporter gene plasmid regulated by cAMP response elements are co-transfected into HEK293 cells. When the compound binds to the receptor and activates the receptors, the expression of the luciferase will increase. The activation status of the compound to GLP1R can be learned by testing the activity of the luciferase.

| No. of the test drug: | amount (mg) | DMSO (μl) | Final concentration (mM) |
|---|---|---|---|
| Liraglutide | 2 | 53.31556 | 10 |
| HS-20001 | 2 | 43.81871 | 10 |
| HS-20002 | 2 | 43.91502 | 10 |

-continued

| No. of the test drug: | amount (mg) | DMSO (μl) | Final concentration (mM) |
|---|---|---|---|
| HS-20003 | 2 | 44.99387 | 10 |
| HS-20004 | 2 | 44.8526 | 10 |
| HS-20005 | 2 | 43.81871 | 10 |
| HS-20006 | 2 | 43.91502 | 10 |
| HS-20007 | 2 | 44.99387 | 10 |
| HS-20008 | 2 | 44.8526 | 10 |

Experimental Procedures:

1. HEK293 cells stably transfected with GLP1R and pCRE-Luc plasmid were implanted in 96 well plate with the amount 40000 cells/well/100 μl, and incubated at 37° C. for 24 hours.

2. The compounds or positive drugs having a certain concentration gradient were added (3 wells per concentration) and incubated at 37° C. for 5 hours. The negative control was solvent DMSO.

3. 50 μl culture medium was taken from each well, and 50 μl of the luciferase substrate were added and vortexed for 10 minutes.

4. 80 μl reaction solution was taken and transferred to a white 96 well plate, then detected on the Invision microplate reader (enzyme-labelling measuring instrument).

The experimental results: compared with positive compounds liraglutide, the activity of the compound HS-20001 is approximately equal to that of the positive compounds, but HS-20002-20008 show much better agonist activity.

TABLE 1

EC50 Values of the series of compounds:

| Compounds | EC50 (nM) | 95% CI (nM) | Maximum reaction rate (%) |
|---|---|---|---|
| Liraglutide | 0.014707 | 9.726e−012 to 2.223e−011 | 96.84616 |
| HS-20001 | 0.013552 | 7.6757e−012 to 2.3963e−011 | 98.11013 |
| HS-20002 | 0.0014145 | 1.2036e−012 to 1.6623e−012 | 87.99447 |
| HS-20003 | 0.00071876 | 4.9657e−013 to 1.0404e−012 | 87.86082 |
| HS-20004 | 0.00037259 | 2.1453e−013 to 6.4710e−013 | 90.81368 |
| HS-20005 | 0.00023552 | 7.3567e−012 to 2.2346e−011 | 89.13468 |
| HS-20006 | 0.00064358 | 1.3581e−012 to 1.4523e−012 | 87.4281 |
| HS-20007 | 0.00054921 | 4.1354e−013 to 1.2514e−012 | 87.0389 |
| HS-20008 | 0.00021002 | 2.2436e−013 to 6.0245e−013 | 88.4628 |

Experimental Example 2

Test In Vivo Activity db/db mice with type 2 diabetes were divided into six groups based on a random blood glucose and body weight (8 per group). Physiological saline, 3 or 10 μg/kg HS series new compounds (Liraglutide, 20001, 20002, 20003, 20004, 20005, 20006, 20007, 20008) are administered by single subcutaneous injection. The random blood glucose of the mice is determined at differete time after administration.

The animals used in the experiment are db/db mice, which are products of a U.S. corporation named Jackson and are conserved and reproduced by Shanghai Institute of Materia Medica of Chinese Academy of Science, of which the Certificate of Conformity is: SCXK(HU)2008-0017, Body Weight: 35-50 g; Gender: Male 85, female 86, bred in SPF-grade animal room; Temperature: 22-24° C.; Humidity: 45-80%; Light: 150-300Lx, 12 h day alternates with night.

The test candidates of the experiment are HS-20001, HS-20002, HS-20003, HS-20004, HS-20005, HS-20006, HS-20007, HS-20008, liraglutide (developed by Novo Nordisk, as Positive control).

Preparation method: 1 bottle of the compound (2 mg/bottle) was dissolved with double-distilled water to prepare a colorless and transparent solution of which the concentration is 2 mg/mL. Then the solution was diluted to 0.6 μg/mL and 2 μg/mL with physiological saline (Sodium chloride injection, Double-Crane Pharmaceutical Co., Ltd. Anhui, batch number: 080728 6C). "ACCU-CHEK® Advantage" blood glucose meter form Roche was used to determine the blood glucose.

Dose Setting and Group
Test Group 1:
Control group: physiological saline
Liraglutide group 3 μg/kg
HS-20001group: 3 μg/kg
HS-20002group: 3 μg/kg
HS-20003group: 3 μg/kg
HS-20004group: 3 μg/kg
HS-20005group: 3 μg/kg
HS-20006group: 3 μg/kg
HS-20007group: 3 μg/kg
HS-20008group: 3 μg/kg
Test Group 2:
Control group: physiological saline
Liraglutide group: 10 μg/kg
HS-20001group: 10 μg/kg
HS-20002group: 10 μg/kg
HS-20003group: 10 μg/kg
HS-20004group: 10 μg/kg
HS-20005group: 10 μg/kg
HS-20006group: 10 μg/kg
HS-20007group: 10 μg/kg
HS-20008group: 10 μg/kg Route and volume of administration: Single subcutaneous injection dose, dose volume was 5 mL/kg.

Test Method

Screening, Grouping, and Administration for db/db Mice with Type 2 Diabetes

Test Group 1:

171 db/db mice (male 85, female 86) were single-cage reared after weaning, fed with high fat diet. The random and fasting blood glucoses were measured after the db/db mice were seven weeks old. 80 db/db mice which fall ill were picked out and divided into 10 groups according to random blood glucose. Fasting blood glucose and body weight as follows: model control group, Liraglutide group-3 μg/kg, HS-20001 group-3 μg/kg, HS-20002 group-3 μg/kg, HS-20003 group-3 μg/kg, HS-20004 group-3 μg/kg, HS-20005 group-3 μg/kg, HS-20006 group-3 μg/kg, HS-20007 group-3 μg/kg and HS-20008 group-3 μg/kg.

Test Group 2:

The random blood glucoses of db/db mice were measured. 80 db/db mice which fall ill were picked out and are divided into 10 groups according to random blood glucose and body weight as follows: model control group, Liraglutide group-10 μg/kg, HS-20001 group-10 μg/kg, HS-20002 group-10 μg/kg, HS-20003 group-10 μg/kg, HS-20004 group-10 μg/kg, HS-20005 group-10 μg/kg, HS-20006 group-10 μg/kg, HS-20007 group-10 μg/kg and HS-20008 group-10 μg/kg.

Each group has 8 mice, half male and half female. The animals of each group were administered with the test compounds or solvent control respectively through single subcutaneous injection. The random blood glucose was determined at 1 h, 2 h, 4 h, 8 h and 24 h after administration, and the decrease rate of blood glucose as calculated as follows:

Decrease rate of blood glucose=(blood glucose of contro group1–blood glucose of treatment group)/blood glucose of control group*100%.

The Experimental Results

Test 1: Effect of the low-dose new compounds administered by singe dose on random blood glucose of db/db mice The results can be seen in Tables 2 and 3. db/db mice were administered with 3 μg/kg HS-20002, 20004, 20005, 20006, 20007, or 20008 through single subcutaneous injection. After one hour, random blood glucose values of the mice were decreased significantly compared with those of the control group (P<0.05). Decrease rates are 24.51%, 15.00%, 14.00%, 14.25%, 13.98% and 13.90% respectively. After 2 h and 4 h from administration, random blood glucose values kept a lower level and had significant difference from those of the control group (P<0.05). After 8 hours from administration, random blood glucose values had no significant difference from those of the control group. The mice were administered with 3 μg/kg HS-20003 through subcutaneous injection. After one hour, random blood glucose values were decreased significantly compared with those of the control group (P<0.05); up to 17.33%, after 2 h, 4 h and 8 h from the administration, random blood glucose values showed no significant difference from those of the control group. After administered with 3 μg/kg HS-20001 for db/db mice through single subcutaneous injection, random blood glucose values decreased and were compared to those of the control group No significant difference was observed. The values of random blood glucose of the group of mice administered with liraglutide had no significant decrease.

TABLE 2

Effect of the administration of the new compounds (mmol/L, $\overline{X} \pm s$, n = 8) through single dose on random blood glucose of db/db mice in the same day.

| groups | Before administration | Time after administration (h) | | | |
|---|---|---|---|---|---|
| | | 1 | 2 | 4 | 8 |
| control | 25.14 ± 1.09 | 23.66 ± 0.73 | 22.63 ± 0.97 | 22.00 ± 1.00 | 25.39 ± 1.08 |
| Liraglutide-3 μg/kg | 25.11 ± 2.33 | 21.78 ± 2.31 | 23.15 ± 2.62 | 21.56 ± 1.37 | 23.93 ± 2.09 |
| HS-20001-3 μg/kg | 25.21 ± 1.44 | 20.34 ± 2.29 | 19.84 ± 1.76 | 20.74 ± 2.51 | 24.29 ± 1.60 |
| HS-20002-3 μg/kg | 25.25 ± 1.57 | 17.86 ± 1.90* | 19.56 ± 0.90* | 18.10 ± 0.79** | 24.19 ± 1.79 |
| HS-20003-3 μg/kg | 25.16 ± 1.49 | 19.56 ± 1.19* | 19.44 ± 1.48 | 19.63 ± 1.12 | 22.59 ± 1.05 |
| HS-20004-3 μg/kg | 25.11 ± 1.63 | 20.11 ± 1.28* | 18.81 ± 1.50* | 17.98 ± 1.38* | 23.30 ± 1.47 |

TABLE 2-continued

Effect of the administration of the new compounds (mmol/L, $\overline{X} \pm s$, n = 8) through single dose on random blood glucose of db/db mice in the same day.

| groups | Before administration | Time after administration (h) | | | |
|---|---|---|---|---|---|
| | | 1 | 2 | 4 | 8 |
| HS-20005-3 µg/kg | 25.21 ± 1.56 | 20.11 ± 1.19* | 18.96 ± 1.50* | 18.98 ± 1.48* | 22.36 ± 1.67 |
| HS-20006-3 µg/kg | 25.11 ± 1.49 | 20.36 ± 1.25* | 19.91 ± 1.70* | 19.58 ± 1.54* | 24.30 ± 1.50 |
| HS-20007-3 µg/kg | 25.16 ± 1.63 | 20.43 ± 1.19* | 19.81 ± 1.610* | 20.98 ± 2.38* | 23.42 ± 1.38 |
| HS-20008-3 µg/kg | 25.11 ± 1.58 | 20.56 ± 1.30* | 20.81 ± 1.70* | 19.30 ± 2.02* | 22.41 ± 1.51 |

*P < 0.05,
**P < 0.01, Compared with those of the control group

TABLE 3

The decrease rate of random blood glucose (%, n = 8) of db/db mice administered with the new compounds through single dose in the same day

| group | Time after administration (h) | | | |
|---|---|---|---|---|
| | 1 | 2 | 4 | 8 |
| Liraglutide-3 µg/kg | 7.98% | −2.32% | 1.99% | 5.76% |
| HS-20001-3 µg/kg | 14.05% | 12.32% | 5.74% | 4.33% |
| HS-20002-3 µg/kg | 24.51% | 13.54% | 17.73% | 4.73% |
| HS-20003-3 µg/kg | 17.33% | 14.09% | 10.80% | 11.03% |
| HS-20004-3 µg/kg | 15.00% | 16.85% | 18.30% | 8.22% |
| HS-20005-3 µg/kg | 14.00% | 12.87% | 10.53% | 8.02% |
| HS-20006-3 µg/kg | 14.25% | 13.12% | 10.86% | 8.14% |
| HS-20007-3 µg/kg | 13.98% | 11.85% | 9.30% | 6.54% |
| HS-20008-3 µg/kg | 13.90% | 11.62% | 8.90% | 6.25% |

Test 2: Effect of the high-dose new compounds administered by single dose on random blood glucose of db/db mice The results can be seen in Tables 4 and 5. db/db mice were administered with 10 µg/kg HS-20002 through single subcutaneous injection. After one hour, the random blood glucose values of the mice decreased significantly compared with those of the control group (P<0.01). After 2 h, 4 h and 8 h from the administration, the random blood glucose values kept a lower level, wherein the values at 4 h after administration were most obvious, of which the decrease rate is up to 40.67% and is significantly different from that of the control group (P<0.001), until 24 hours after administration, the random blood glucose values were still significantly lower than those of the control group. The mice were administered with 10 µg/kg HS-20003 through single subcutaneous injection. After one hour, the random blood glucose values were decreased significantly compared with those of the control group (P<0.01) and is up to 23.62% decreasing, after 2 h, 4 h and 8 h from the administration. The random blood glucose values still keep at a lower level. After 24 hours from administration, there was no significant difference compared with the control group. db/db mice are administered with 10 µg/kg HS-20001 through single subcutaneous injection, after 2 h, the random blood glucose values are decreased significantly compared with those of the control group, after 4 h and 8 h from the administration, the random blood glucose values still keep at a lower level. After 24 hours from administration, the random blood glucose values showed no significant difference from those of the control group. HS-20002, HS-20004, HS-20005, HS-20006, HS-20007 or HS-20008 were administered to mice through single subcutaneous injection and the random blood glucose values are decreased immediately and significantly. The decrease rate is up to 36.20%, after 2 hours. After 4 and 8 hours from the administration, the blood glucose values still kept at a lower level. After 24 hours from the administration, blood glucose was not significantly different compared with those of the control group. The values of random blood glucose of mice of group administered with liraglutide have no significant decrease.

TABLE 4

Effect of the new compounds administered through single dose (mmol/L, ± s, n = 8) on the random blood glucose of db/db mice in the same day.

| Group | Before administration | Time after administration (h) | | | | |
|---|---|---|---|---|---|---|
| | | 1 | 2 | 4 | 8 | 24 |
| Control | 23.08 ± 1.37 | 27.15 ± 1.51 | 28.49 ± 1.58 | 30.76 ± 1.15 | 29.96 ± 0.88 | 27.75 ± 1.64 |
| liraglutide-10 µg/kg | 23.19 ± 1.35 | 28.59 ± 1.50 | 28.89 ± 1.17 | 28.55 ± 1.31 | 31.84 ± 0.65 | 27.78 ± 1.14 |
| HS-20001-10 µg/kg | 23.16 ± 1.57 | 23.90 ± 1.79 | 20.94 ± 1.57** | 20.20 ± 1.78*** | 23.86 ± 1.87* | 24.60 ± 1.92 |
| HS-20002-10 µg/kg | 23.15 ± 1.32 | 19.74 ± 1.16** | 20.31 ± 2.01** | 18.25 ± 1.98*** | 22.55 ± 2.20** | 22.60 ± 1.46* |
| HS-20003-10 µg/kg | 23.20 ± 1.36 | 20.74 ± 0.98** | 21.10 ± 0.80*** | 19.54 ± 1.80*** | 22.14 ± 2.16** | 24.45 ± 1.55 |
| control | 23.08 ± 1.37 | 30.76 ± 1.15 | 30.29 ± 0.98 | 29.90 ± 0.89 | 31.04 ± 0.94 | 28.98 ± 1.62 |
| HS-20004-10 µg/kg | 23.18 ± 1.65 | 19.63 ± 1.81*** | 21.86 ± 1.66*** | 21.44 ± 1.68*** | 23.80 ± 1.46*** | 25.64 ± 1.85 |
| HS-20005-10 µg/kg | 23.64 ± 1.35 | 19.39 ± 1.61*** | 21.56 ± 1.56*** | 21.49 ± 1.34*** | 23.46 ± 1.51*** | 25.52 ± 1.68 |
| HS-20006-10 µg/kg | 23.54 ± 1.39 | 19.52 ± 1.72*** | 21.43 ± 1.49*** | 21.53 ± 1.67*** | 23.39 ± 1.55*** | 25.59 ± 1.74 |
| HS-20007-10 µg/kg | 23.56 ± 1.42 | 19.41 ± 1.54*** | 21.84 ± 1.57*** | 21.64 ± 1.56*** | 23.81 ± 1.67*** | 25.51 ± 1.53 |

TABLE 4-continued

Effect of the new compounds administered through single dose (mmol/L, ± s, n = 8) on the random blood glucose of db/db mice in the same day.

| Group | Before administration | Time after administration (h) | | | | |
|---|---|---|---|---|---|---|
| | | 1 | 2 | 4 | 8 | 24 |
| HS-20008-10 μg/kg | 23.49 ± 1.49 | 19.38 ± 1.83*** | 21.61 ± 1.68*** | 21.72 ± 1.63*** | 23.56 ± 1.80*** | 25.72 ± 1.69 |

*$P < 0.05$,
**$P < 0.01$,
***$P < 0.001$, Compared with the control group

TABLE 5

The decrease rate of the random blood glucose (%, n = 8) of db/db mice administered with the new compounds through single dose in the same day.

| group | Time after administration (h) | | | | |
|---|---|---|---|---|---|
| | 1 | 2 | 4 | 8 | 24 |
| liraglutide-10 μg/kg | −5.29% | −1.40% | 7.19% | −6.26% | −0.09% |
| HS-20001-10 μg/kg | 11.97% | 26.50% | 34.34% | 20.36% | 11.35% |
| HS-20002-10 μg/kg | 27.30% | 28.71% | 40.67% | 24.74% | 18.56% |
| HS-20003-10 μg/kg | 23.62% | 25.93% | 36.49% | 26.12% | 11.89% |
| HS-20004-10 μg/kg | 36.20% | 27.82% | 28.30% | 23.32% | 11.52% |
| HS-20005-10 μg/kg | 37.58% | 28.32% | 29.12% | 24.10% | 12.46% |
| HS-20006-10 μg/kg | 38.12% | 27.66% | 29.78% | 23.72% | 13.66% |
| HS-20007-10 μg/kg | 36.72% | 25.43% | 26.54% | 23.03% | 12.16% |
| HS-20008-10 μg/kg | 35.49% | 25.79% | 27.33% | 22.57% | 14.58% |

Test Conclusions:

The random blood glucose of db/db mice administered with series of the new compounds of the invention through single subcutaneous injection decreased significantly. The random blood glucose level decreased obviously by HS-20002, HS-20003, HS-20004, HS-20005, HS-20006, HS-20007 and HS-20008 in a dose of 3 g/kg. Where, HS-20002 and HS-20004 show a much better effect on reducing random blood glucose, the duration of the hypoglycemic effect after single subcutaneous injection was dose-related. The duration of the effect of HS-20002 and HS-20004 on decreasing random blood glucose in the dose of 3 g/kg was more than 4 hours. The duration of the effect of HS-20001, HS-20002, HS-20003, HS-20004, HS-20005, HS-20006, HS-20007 and HS-20008 on decreasing random blood glucose in the dose of 10 g/kg was more than 8 hours.

What is claimed is:

1. A GLP-1 analogue or a pharmaceutically acceptable salt thereof comprising:
   the amino acid sequence of SEQ ID NO: 237;
   a lipophilic substituent of formula $R_1(CH_2)_n$—CO— that is linked to the amino acid sequence of SEQ ID NO: 237 through an amide bond, where $R_1$ is selected from $CH_3$— and HOOC— and n is an integer selected from 8-25.

2. The GLP-1 analogue or a pharmaceutically acceptable salt thereof of claim 1, wherein the amide bond is formed by the lipophilic substituent of formula $R_1(CH_2)_n$—CO— and an ϵ amino group of the C-terminal Lys residue.

3. The GLP-1 analogue or a pharmaceutically acceptable salt thereof of claim 2, wherein $R_1$ is $CH_3$—.

4. The GLP-1 analogue or a pharmaceutically acceptable salt thereof of claim 3, wherein n is selected from 8, 10, 12, 14, 16, 18, 20, and 22.

5. The GLP-1 analogue or a pharmaceutically acceptable salt thereof of claim 3, wherein n is 14.

6. The GLP-1 analogue or a pharmaceutically acceptable salt thereof of claim 2, wherein $R_1$ is HOOC—.

7. The GLP-1 analogue or a pharmaceutically acceptable salt thereof of claim 6, wherein n is selected from 8, 10, 12, 14, 16, 18, 20, and 22.

8. The GLP-1 analogue or a pharmaceutically acceptable salt thereof of claim 6, wherein n is 14.

9. The GLP-1 analogue or a pharmaceutically acceptable salt thereof of claim 1, wherein the amide bond is formed by the lipophilic substituent of formula $R_1(CH_2)_n$—CO— and an α amino group of the C-terminal Lys residue.

10. The GLP-1 analogue or a pharmaceutically acceptable salt thereof of claim 9, wherein $R_1$ is $CH_3$—.

11. The GLP-1 analogue or a pharmaceutically acceptable salt thereof of claim 10, wherein n is selected from 8, 10, 12, 14, 16, 18, 20, and 22.

12. The GLP-1 analogue or a pharmaceutically acceptable salt thereof of claim 10, wherein n is 14.

13. The GLP-1 analogue or a pharmaceutically acceptable salt thereof of claim 9, wherein $R_1$ is HOOC—.

14. The GLP-1 analogue or a pharmaceutically acceptable salt thereof of claim 13, wherein n is selected from 8, 10, 12, 14, 16, 18, 20, and 22.

15. The GLP-1 analogue or a pharmaceutically acceptable salt thereof of claim 13, wherein n is 14.

16. A GLP-1 analogue or a pharmaceutically acceptable salt thereof comprising:
   the amino acid sequence of SEQ ID NO: 3;
   a lipophilic substituent of formula $R_1(CH_2)_n$—CO— that is linked to the amino acid sequence of SEQ ID NO: 3 through an amide bond, where $R_1$ is selected from $CH_3$— and HOOC— and n is an integer selected from 8-25.

17. A GLP-1 analogue or a pharmaceutically acceptable salt thereof comprising:
   the amino acid sequence of SEQ ID NO: 4;
   a lipophilic substituent of formula $R_1(CH_2)_n$—CO— that is linked to the amino acid sequence of SEQ ID NO: 4 through an amide bond, where $R_1$ is selected from $CH_3$— and HOOC— and n is an integer selected from 8-25.

18. A method of treating non-insulin-dependent diabetes mellitus, or insulin-dependent diabetes, or comprising administering a therapeutically effective amount of a GLP-1 analogue or a pharmaceutically acceptable salt according to claim 1 to a patient in need thereof.

19. A method of treating non-insulin-dependent diabetes mellitus, or insulin-dependent diabetes, or comprising administering a therapeutically effective amount of a GLP-1 analogue or a pharmaceutically acceptable salt according to claim 16 to a patient in need thereof.

20. A method of treating non-insulin-dependent diabetes mellitus, or insulin-dependent diabetes, or comprising administering a therapeutically effective amount of a GLP-1 analogue or a pharmaceutically acceptable salt according to claim 17 to a patient in need thereof.

21. The GLP-1 analogue or a pharmaceutically acceptable salt thereof of claim 16, wherein the amide bond is formed by the lipophilic substituent of formula $R_1(CH_2)_n$—CO— and an ϵ amino group of the C-terminal Lys residue.

22. The GLP-1 analogue or a pharmaceutically acceptable salt thereof of claim 21, wherein $R_1$ is $CH_3$—.

23. The GLP-1 analogue or a pharmaceutically acceptable salt thereof of claim 22, wherein n is selected from 8, 10, 12, 14, 16, 18, 20, and 22.

24. The GLP-1 analogue or a pharmaceutically acceptable salt thereof of claim 22, wherein n is 14.

25. The GLP-1 analogue or a pharmaceutically acceptable salt thereof of claim 21, wherein $R_1$ is HOOC—.

26. The GLP-1 analogue or a pharmaceutically acceptable salt thereof of claim 25, wherein n is selected from 8, 10, 12, 14, 16, 18, 20, and 22.

27. The GLP-1 analogue or a pharmaceutically acceptable salt thereof of claim 25, wherein n is 14.

28. The GLP-1 analogue or a pharmaceutically acceptable salt thereof of claim 16, wherein the amide bond is formed by the lipophilic substituent of formula $R_1(CH_2)_n$—CO— and an α amino group of the C-terminal Lys residue.

29. The GLP-1 analogue or a pharmaceutically acceptable salt thereof of claim 28, wherein $R_1$ is $CH_3$—.

30. The GLP-1 analogue or a pharmaceutically acceptable salt thereof of claim 29, wherein n is selected from 8, 10, 12, 14, 16, 18, 20, and 22.

31. The GLP-1 analogue or a pharmaceutically acceptable salt thereof of claim 29, wherein n is 14.

32. The GLP-1 analogue or a pharmaceutically acceptable salt thereof of claim 28, wherein $R_1$ is HOOC—.

33. The GLP-1 analogue or a pharmaceutically acceptable salt thereof of claim 32, wherein n is selected from 8, 10, 12, 14, 16, 18, 20, and 22.

34. The GLP-1 analogue or a pharmaceutically acceptable salt thereof of claim 33, wherein n is 14.

35. The GLP-1 analogue or a pharmaceutically acceptable salt thereof of claim 17, wherein the amide bond is formed by the lipophilic substituent of formula $R_1(CH_2)_n$—CO— and an ϵ amino group of the C-terminal Lys residue.

36. The GLP-1 analogue or a pharmaceutically acceptable salt thereof of claim 35, wherein $R_1$ is $CH_3$—.

37. The GLP-1 analogue or a pharmaceutically acceptable salt thereof of claim 36, wherein n is selected from 8, 10, 12, 14, 16, 18, 20, and 22.

38. The GLP-1 analogue or a pharmaceutically acceptable salt thereof of claim 36, wherein n is 14.

39. The GLP-1 analogue or a pharmaceutically acceptable salt thereof of claim 35, wherein $R_1$ is HOOC—.

40. The GLP-1 analogue or a pharmaceutically acceptable salt thereof of claim 39, wherein n is selected from 8, 10, 12, 14, 16, 18, 20, and 22.

41. The GLP-1 analogue or a pharmaceutically acceptable salt thereof of claim 39, wherein n is 14.

42. The GLP-1 analogue or a pharmaceutically acceptable salt thereof of claim 17, wherein the amide bond is formed by the lipophilic substituent of formula $R_1(CH_2)_n$—CO— and an α amino group of the C-terminal Lys residue.

43. The GLP-1 analogue or a pharmaceutically acceptable salt thereof of claim 42, wherein $R_1$ is $CH_3$—.

44. The GLP-1 analogue or a pharmaceutically acceptable salt thereof of claim 43, wherein n is selected from 8, 10, 12, 14, 16, 18, 20, and 22.

45. The GLP-1 analogue or a pharmaceutically acceptable salt thereof of claim 43, wherein n is 14.

46. The GLP-1 analogue or a pharmaceutically acceptable salt thereof of claim 42, wherein $R_1$ is HOOC—.

47. The GLP-1 analogue or a pharmaceutically acceptable salt thereof of claim 46, wherein n is selected from 8, 10, 12, 14, 16, 18, 20, and 22.

48. The GLP-1 analogue or a pharmaceutically acceptable salt thereof of claim 47, wherein n is 14.

49. A method of treating non-insulin-dependent diabetes mellitus, or insulin-dependent diabetes, or comprising administering a therapeutically effective amount of a GLP-1 analogue or a pharmaceutically acceptable salt according to claim 15 to a patient in need thereof.

50. A method of treating non-insulin-dependent diabetes mellitus, or insulin-dependent diabetes, or comprising administering a therapeutically effective amount of a GLP-1 analogue or a pharmaceutically acceptable salt according to claim 34 to a patient in need thereof.

51. A method of treating non-insulin-dependent diabetes mellitus, or insulin-dependent diabetes, or comprising administering a therapeutically effective amount of a GLP-1 analogue or a pharmaceutically acceptable salt according to claim 48 to a patient in need thereof.

* * * * *